United States Patent [19]
Yano et al.

[11] Patent Number: 5,872,272
[45] Date of Patent: Feb. 16, 1999

[54] POLYVALENT METAL SALTS OF PHOSPHORIC DIESTER AND ORGANO(POLY)SILOXANES MODIFIED WITH POLYVALENT METAL SALT OF PHOSPHORIC DIESTER

[75] Inventors: Shinji Yano, Naga-gun; Junichi Fukasawa, Wakayama; Hironori Kawasaki, Ichikai-machi; Munehisa Okutsu; Takeshi Ihara, both of Wakayama; Katsumi Kita, Izumisano; Yoshiaki Fujikura, Utsunomiya; Akira Akaogi, Machida, all of Japan

[73] Assignee: Kao Corporation, Tokyo, Japan

[21] Appl. No.: 454,181

[22] PCT Filed: Dec. 28, 1993

[86] PCT No.: PCT/JP93/01924

§ 371 Date: Jun. 15, 1995

§ 102(e) Date: Jun. 15, 1995

[87] PCT Pub. No.: WO94/14822

PCT Pub. Date: Jul. 7, 1994

[30] Foreign Application Priority Data

Dec. 28, 1992 [JP] Japan .................. 4-348616
Jan. 28, 1993 [JP] Japan .................. 5-012862
Mar. 23, 1993 [JP] Japan .................. 5-064209
Sep. 28, 1993 [JP] Japan .................. 5-241264
Oct. 6, 1993 [JP] Japan .................. 5-250336

[51] Int. Cl.$^6$ .................................................. C07F 7/08
[52] U.S. Cl. ........................ 556/12; 556/405; 556/14; 556/24; 556/174; 252/315.1; 252/70; 252/166; 252/83; 424/70.1; 424/70.4; 424/70.12; 260/665 R

[58] Field of Search .................. 556/405, 12, 14, 556/174, 24; 252/315.1, 70, 166, 83; 424/70.1, 70.4, 70.12; 260/665 R Primary Examiner—Paul F. Shaver
Attorney, Agent, or Firm—Oblon, Spivak, McClelland, Maier & Neustadt, P.C.

[57] ABSTRACT

The present invention relates to polyvalent metal salts of a phosphoric diester represented by formula (1) and organo (poly)siloxanes modified with a polyvalent metal salt of a phosphoric diester having the structural units represented by formulae (9) and (10):

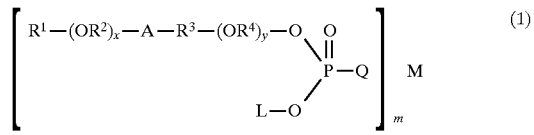

wherein $R^1$ represents a C1 to C20 linear or branched alkyl group, $R^2$ and $R^4$ are the same or different and independently represent a C2 to C3 linear or branched alkylene group, $R^3$ represents a C3 to C20 linear or C5 to C20 branched alkylene group, A represents a group —COO— or —O—, x and y are the same or different from each other and independently represent an integer of 0 to 10, L represents a C1 to C40 linear or branched alkyl group or a group, $R^1$—$(OR^2)_x$—A—$R^3(OR^4)_y$— wherein $R^1$, $R^2$, $R^3$, $R^4$, A, x and y have the same meaning as defined herein before, M represents a divalent or polyvalent metal atom, and m represents the same value as the valence of M.

19 Claims, No Drawings

POLYVALENT METAL SALTS OF PHOSPHORIC DIESTER AND ORGANO(POLY)SILOXANES MODIFIED WITH POLYVALENT METAL SALT OF PHOSPHORIC DIESTER

TECHNICAL FIELD

The present invention relates to polyvalent metal salts of a phosphoric diester or organo(poly)siloxanes modified with a polyvalent metal salt of a phosphoric diester which are useful as starting materials in the manufacture of perfumery and cosmetic compositions. The present invention also relates to processes for manufacturing the salts or the organo(poly)siloxanes, gelling agents containing the same and cosmetic compositions containing the same, which provide excellent sensation during use and have a good stability.

DESCRIPTION OF THE RELATED ART

Conventional oil-based cosmetic compositions are either in a liquid state or in a solid (wax) state, and therefore, they entail drawbacks in handling, such as running of liquid and difficulty in taking out the content from the container. These drawbacks would be overcome by the use of gelling agents which are capable of providing oil-based cosmetic compositions with proper viscosity. From this point of view, many approaches have been proposed to apply materials known as oil gelling agents to cosmetic compositions.

Among such gelling agents, metallic soap, dextrin fatty acid esters, metal salts of dialkyl phosphoric esters and the like involve drawbacks in that they become brittle and hard gels when they are cooled down at a temperature not higher than a phase inversion temperature (hereinafter referred to as Tc) after heated and dissolved in oil, and the gels cannot be recovered upon stress. In order to recover the gels, it was necessary to heat them again at a temperature not lower than Tc. To obtain thixotropy sufficient for overcoming this problem, use of compounds having a short-chain branched alkyl group and having a Tc not higher than room temperature is suggested. However, gels of such compounds are highly viscous and have spinnability, resulting in very sticky cosmetic compositions which also raise drawbacks in handling. Organic modified bentonites are capable of imparting sufficient thixotropy to oil-based cosmetic compositions, which however, raise problems in that the additives in the cosmetic composition are freeing, and gels having softness and elasticity are not formed.

Accordingly, development of cosmetic compositions which have sufficient thixotropy, are easy to handle, stable and provide excellent sensation during use has still been desired.

Silicones are known to be resistant against heat, acidity, weather and the like, due to the high bonding energy of its backbone chain. They are also known to have properties of easy release from molds, high lubricity and water repellency due to their low surface tension. Furthermore, small intermolecular force of silicones results in an elastic backbone chain, achieving high gas permeability, and physiologically inert property of silicones features low toxicity and low irritability. Accordingly, silicones have conventionally been utilized in a variety of fields including electric, electronics, automobiles, machines, medicines, cosmetics, fibers, papers, pulps, building materials, and the like.

Especially in the fields of perfumery and cosmetic compositions, dimethylpolysiloxanes and cyclic silicones are actively incorporated into styling agents for the hair and cosmetic compositions as an oil ingredient due to their stickiness-free property and safety. Thus, technology of taking advantage of excellent characteristics of silicone oils and development of their use especially in perfumery and cosmetic compositions have been continued.

Although silicone oils are an important material as a component of perfumery and cosmetic compositions, they still involve problems in manufacturing products of enhanced functions. For example, silicone oils do not have good compatibility with other cosmetic oil base. Accordingly, uniform solutions and stable products having a silicone oil base are difficult to obtain. That is, silicone oils easily leach out and cause separation. Moreover, since there are no agents that are capable of controlling the viscosity of silicone oils, cosmetic compositions containing abundant silicone oils generally have a low viscosity, and entail many problems of poor stability, running of liquid during use, and so on. In the case where silicone oils are used in perfumery or in oil bases of cosmetics, another problem was noted in that stable dispersion of substances having different specific gravities cannot be secured as time passes.

In order to solve the above-mentioned drawbacks, studies have been conducted to make a silicone oil gel and incorporate it into perfumery and bases of cosmetic compositions (see, for example, Japanese Patent Application Laid-open (Kokai) No. 152308/1988, Japanese Patent Application Laid-open (Kokai) No. 190757/1989 and Japanese Patent Application Laid-open (Kokai) No. 207354/1989).

However, these conventional methods all utilize, as an gelling agent, organoplysiloxane polymers which are not soluble in silicone oils but swell therein. These polymers provide gels of excellent stability, but the gels do not have sufficient thixotropic rheology. The property of thixotropic rheology is an important factor required for improving handling and sensation during use of products in the fields of perfumery and cosmetic compositions.

Accordingly, novel gelling agents which avail themselves of the properties of oils, in particular, silicone oils, can impart thixotropic rheology property, provide transparent products of high stability with good sensation during use and free of spinnability have been desired.

DISCLOSURE OF THE INVENTION

The present invention is to provide polyvalent metal salts of a phosphoric diester represented by formula (1):

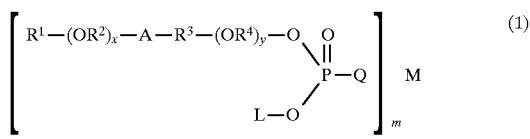

wherein $R^1$ represents a C1 to C20 linear or branched alkyl group, $R^2$ and $R^4$ are the same or different and independently represent a C2 to C3 linear or branched alkylene group, $R^3$ represents a C3 to C20 linear or C5 to C20 branched alkylene group, A represents a group —COO— or —O—, x and y are the same or different from each other and independently represent an integer of 0 to 10, L represents a C1 to C40 linear or branched alkyl group or a group, $R^1$—$(OR^2)_x$—A—$R^3$—$(OR^4)_y$— wherein $R^1$, $R^2$, $R^3$, $R^4$, A, x and y have the same meaning as defined hereinbefore, M represents a divalent or polyvalent (i.e., trivalent or higher) metal ion, and m represents the same value as the valence of M.

In the preparation of these polyvalent metal salts of phosphoric diesters (1), phosphoric diesters represented by formula (2) which will be described later are used. Of the diesters of formula (2), those where $R^3$ is a C7 to C20 linear or branched alkylene are novel compounds.

Accordingly, the present invention also provides phosphoric diesters represented by formula (2'), salts thereof and processes for preparing the same.

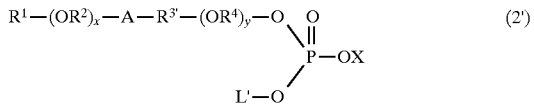

wherein $R^1$, $R^2$, $R^4$, x and y have the same meaning as defined hereinbefore, $R^{3'}$ represents a C7 to C20 linear or branched alkylene group, L' represents a C1 to C40 linear or branched alkyl group or a group, $R^1$—$(OR^2)_x$—A—$R^{3'}$—$(OR^4)_y$— wherein $R^1$, $R^2$, $R^{3'}$, $R^4$, A, x and y have the same meaning as defined hereinbefore, X represents hydrogen, alkali metal, ammonium, alkylamine or alkanolamine.

The present invention also provides cosmetic compositions containing a polyvalent metal salt of phosphoric diester (1).

The present invention furthermore provides organo(poly)siloxanes which are modified with a polyvalent metal salt of phosphoric diester, said siloxanes having structural units represented by formulae (9) and (10), and processes of preparing the same.

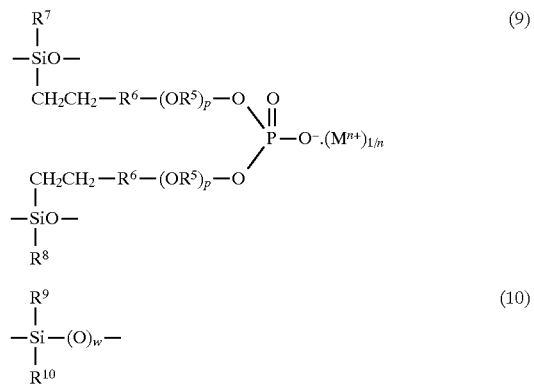

wherein
$R^5$: a C2 to C20 alkylene group,
$R^6$: a C1 to C50 linear or branched alkylene group which may optionally be substituted by a hydroxyl group,
p: a number from 0 to 200,
M: a polyvalent metal atom of divalent or polyvalent,
n: a number same as the value of the valence of M,
$R^7$, $R^8$, $R^9$, $R^{10}$: independently represent a hydrogen atom, an alkyl group, an alkoxy group, a phenyl group or a structural unit represented by formula (10), and
w: a number of 0 or 1.

The present invention furthermore provides cosmetic compositions which contain the organo(poly)siloxane modified with a polyvalent metal salt of phosphoric diester.

The cosmetic compositions containing the organo(poly) siloxane modified with a polyvalent metal salt of phosphoric diester represented by formula (1) according to the present invention have sufficient thixotropy while exhibiting no spinnability, are transparent, stable, and are excellent in sensation during use.

Moreover, the organo(poly)siloxane modified with a polyvalent metal salt of phosphoric diester according to the present invention are capable of imparting thixotropic rheological property to silicone oils to be incorporated in a variety of cosmetic compositions and perfumery, of constituting gels which are highly safe, transparent, excellent in sensation during use, and free of spinnability, and therefore, cosmetic compositions containing the same can give a non-sticky and refreshing sensation to users, are stable as time passes, and running of liquid can be prevented even though abundant silicone oils are present.

BEST MODE FOR CARRYING OUT THE INVENTION

The polyvalent metal salts of a phosphoric diester according to the present invention are represented by formula (1) as described hereinbefore. Specific examples of $R^1$, which is a C1 to C20, preferably C4 to C10 linear or branched alkyl group, include methyl, ethyl, n-propyl, isopropyl, n-butyl, isobutyl, t-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosadecyl, neopentyl, 2-ethylhexyl, 3,3-dimethylbutyl, 1,1,3,3-tetramethylbutyl, 3,7-dimethyloctyl, 3,7-dimethyloctane-3-yl, 2-hexyldecyl, 2-heptylundecyl, 2-octyldodecyl, 3,7,11-trimethyldodecyl, 3,7,11,15-tetramethylhexadecyl, 3,5,5-trimethylhexyl, 2,3,4-trimethylpentan-3-yl, 2,3,4,6,6-pentamethylheptan-3-yl and isostearyl, and particularly t-butyl is most preferable since it has an excellent ability in its gelling effect on silicone oils.

Specific examples of C2 to C3 linear or branched alkylene groups represented by $R^2$ and $R^4$ include ethylene and methylethylene. Preferable examples of the integars of x and y are 0 to 5. Specific examples of C3 to C20 linear or C5 to C20 branched alkylene groups represented by $R^3$ include trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene, eicosadecamethylene, 3-methylpentan-1,5-diyl, 2-ethylhexane-1,6-diyl, 3,7-dimethyloctane-1,8-diyl and 3,7-dimethyloctane-3,8-diyl, with C4 to C9 lenear or C5 to C9 branched alkylene groups being preferred.

Moreover, among the groups represented by L, specific examples of C1 to C40 linear or branched alkyl group include C1 to C20 alkyl described hereinbefore, 2-dodecylhexadecyl, 2-tetradecyloctadecyl and 2-hexadecyleicosyl, with C4 to C20 lenear or branched alkyl groups being preferred.

Specific examples of divalent or polyvalent metal atoms Ca, Al, Fe (III), Fe (II), Ba, Ti, Zn and Zr, among which Ca and Al are particularly preferred.

These polyvalent metal salts (1) of phosphoric diester according to the present invention are prepared, for example, by reacting a polyvalent metal salt represented by formula (3):

wherein M has the same meaning as defined hereinbefore, Y represents an organic or inorganic anion, p and q are integers which correspond to the valence of Y and m, respectively and are minimum ratios; with a phosphoric diester represented by formula (2) or a salt thereof:

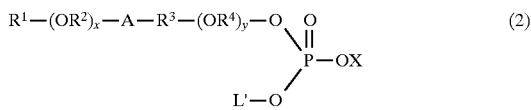  (2)

wherein $R^1$, $R^2$, $R^3$, $R^4$, A, L, x and y have the same meaning as defined hereinbefore, X represents hydrogen, alkali metal, ammonium, alkyl amine or alkanolamine.

The phosphoric diesters and salts thereof represented by formula (2) which are useful in the present invention are prepared, for example, by reacting an alcohol represented by formula (4):

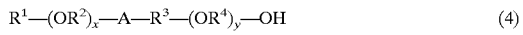  (4)

wherein $R^1$, $R^2$, $R^3$, $R^4$, A, x and y have the same meaning as defined hereinbefore, or a mixture of an alcohol represented by formula (4) and an alcohol represented by formula (5)

L"—OH  (5)

wherein L" represents a C1 to C40 linear or branched alkyl group, with a phosphorylating agent, followed by neutralizing with a monovalent base as desired.

The alcohols represented by formula (4) are prepared, for example, by reacting an alcohol represented by formula (6) or a carboxylic acid represented by formula (7):

  (6)

  (7)

wherein $R^1$, $R^2$ and x have the same meaning as defined hereinbefore; with a halogenating agent such as thionyl chloride, thionyl bromide, phosphorus trichloride, phosphorus pentachloride, phosphorus tribromide, phosphorus pentabromide, hydrogen chloride and hydrogen bromide, to obtain a corresponding halogenated product, with which an excessive amount of diol represented by formula (8):

  (8)

wherein $R^3$, $R^4$ and y have the same meaning as defined hereinbefore is reacted in an inert solvent such as toluene and xylene in the presence of a base such as sodium hydroxide or the like.

Examples of the phosphorylating agents to be reacted with the mentioned alcohols include phosphorus pentaoxide; phosphorus oxyhalides such as phosphorus oxychloride; and polyphosphoric acids.

When phosphorus pentaoxide is used as a phosphorylating agent, alcohol (4) or a mixture of alcohol (4) and alcohol (5) is reacted with a 1 to 0.1 mol fold, preferably 0.5 to 0.2 mol fold of phosphorus pentaoxide at 50° to 90° C. for 3 to 15 hours.

When phosphorus oxyhalides are used as a phosphorylating agent, alcohol (4) or a mixture of alcohol (4) and alcohol (5) is reacted with a 1 to 0.1 mol fold, preferably 0.6 to 0.4 mol fold of phosphorus oxyhalides at −60° to 30° C., preferably at −40° to 10° C. for 1 to 36 hours. If necessary, solvents such as tetrahydrofuran and ethers, and tertiary amines such as triethylamine and pyridine may optionally be added.

After completion of the reaction, 1 to 2 fold equivalent of water based on the phosphorus oxyhalide was added to the reaction mixture for a complete hydrolysis of the phosphorus oxyhalide to obtain phosphoric diester (2).

In this reaction, pyro-phosphoric monoesters and the like are by-produced together with the target phosphoric diester. Therefore, when phosphoric diesters of higher purity are desired, a purifying process as disclosed, for example, in Japanese Patent Publication (Kokoku) No. 29195/1989 may be followed, in which the reaction mixture is added with water for carrying out hydrolysis in an acidic condition, subsequently a base is added thereto for hydrolizing again to convert the phosphoric monoesters into orthophosphoric acid and organic hydroxy compounds, which are removed from the reaction system.

Furthermore, when a mixture of alcohol (4) and alcohol (5) is used, alcohol (4) may first be used to obtain a phosphoric monoester, and then alcohol (5) is reacted thereto to obtain a phosphoric diester.

The thus obtained phosphoric diester can be converted into a salt form by neutralizing with a monovalent base as desired. Examples of the monovalent base include hydroxides and carbonates of alkali metals, ammonia, alkylamine and alkanolamine. More specifically, sodium hydroxide, potassium hydroxide, sodium carbonate, sodium hydrogencarbonate, ammonia, triethylamine and triethanolamine are exemplified, and among them, sodium, hydroxide, potassium hydroxide and triethanolamine are preferred.

Polyvalent metal salts (3) to be reacted with the thus obtained phosphoric diesters or their salts (2) include calcium acetate, aluminum acetate, barium acetate, calcium chloride, calcium carbonate, aluminum sulfate, aluminum chloride, ferric chloride, magnesium acetate, aluminum nitrate and ferric perchlorate, among which calcium acetate, aluminum acetate, calcium chloride and aluminum chloride are particularly preferred.

The reaction is carried out by mixing a polyvalent metal salt (3) in an amount of 1/10 to 10 fold, preferably from 1 to 2 fold based on phosphoric diester or a salt thereof (2) in 1 to 100 fold, preferably 2 to 20 fold of a polar solvent at 20° to 80° C. for 1 to 6 hours under stirring. No limitation is imposed on the polar solvent, but solvents which can dissolve phosphoric diesters and their salts are preferred. Examples of such solvents include water, tetrahydrofuran, methylalcohol, ethylalcohol and acetone. They may be used singly or in combination of two or more.

After completion of the reaction, if the target compounds are deposited as crystals, filtration is carried out for collecting the crystals. If the target compounds are dissolved, a solvent such as hexane, ether or ethyl acetate is added thereto and extraction is carried out, or acetone or the like are added for allowing the target compounds precipitated.

Preferable examples of the thus obtained compounds (1) according to the present invention include the following (1-1) to (1-33).

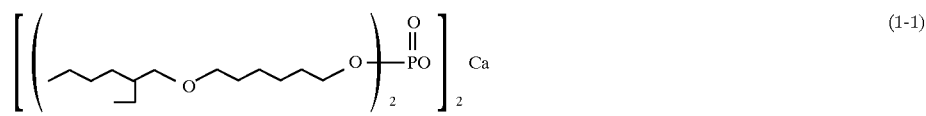  (1-1)

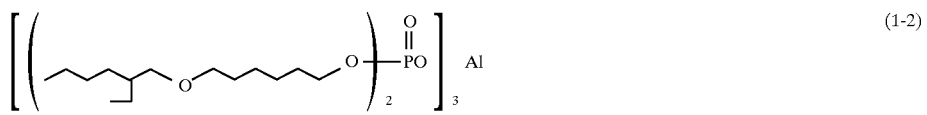 (1-2)
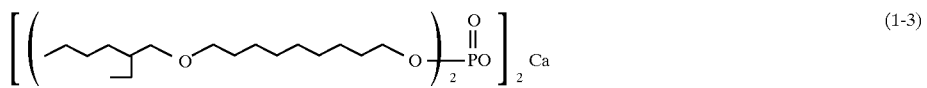 (1-3)
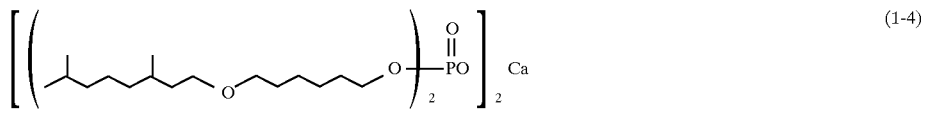 (1-4)
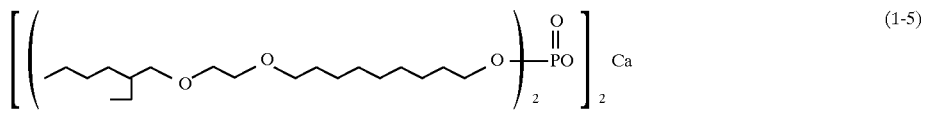 (1-5)
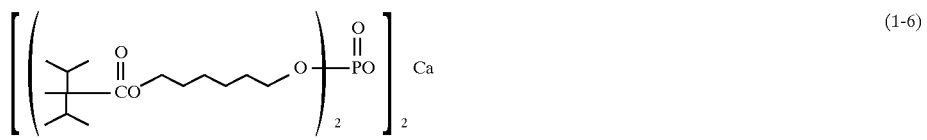 (1-6)
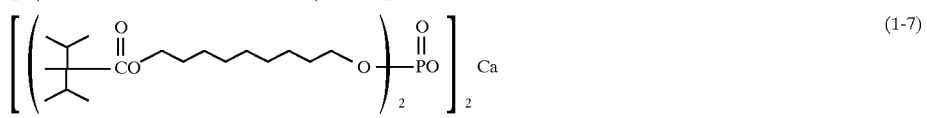 (1-7)
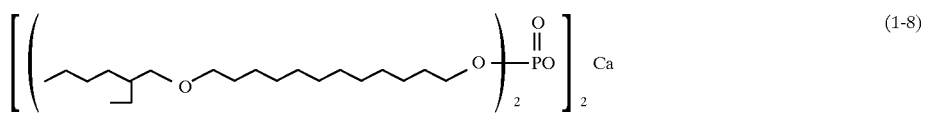 (1-8)
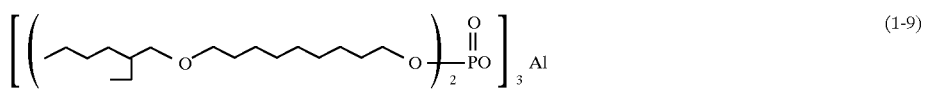 (1-9)
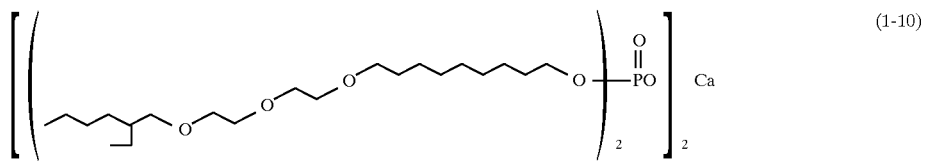 (1-10)
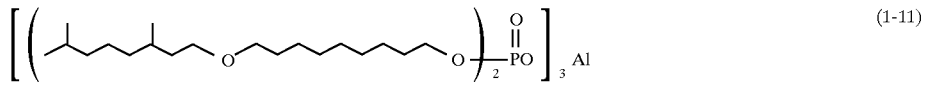 (1-11)
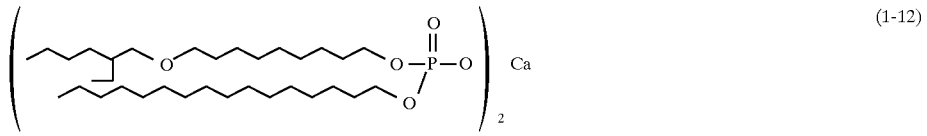 (1-12)
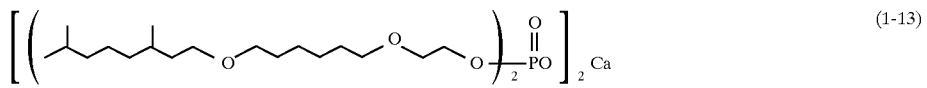 (1-13)
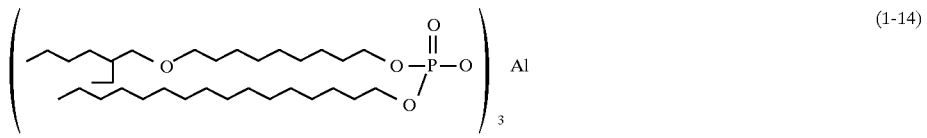 (1-14)
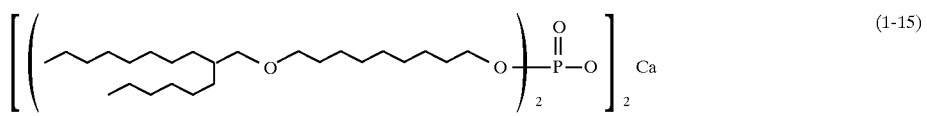 (1-15)
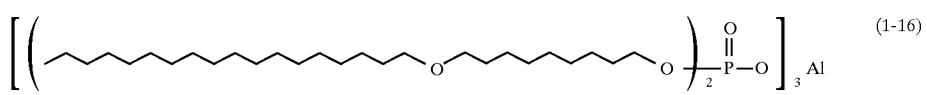 (1-16)

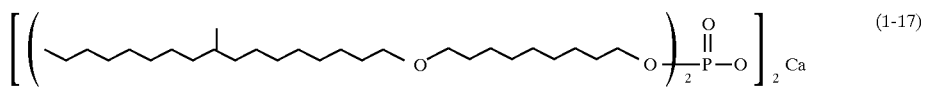
(1-17)
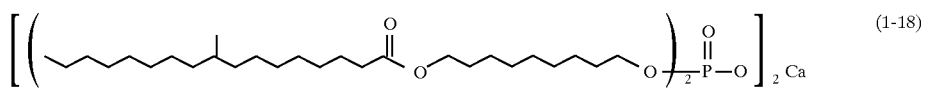
(1-18)
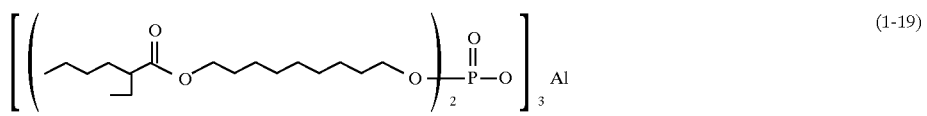
(1-19)
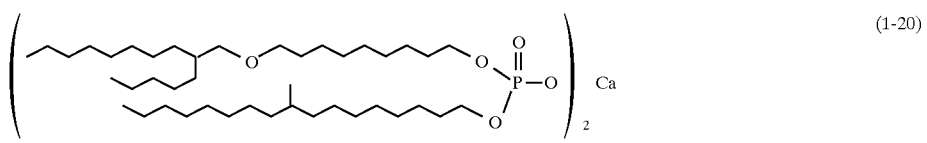
(1-20)
(1-21)
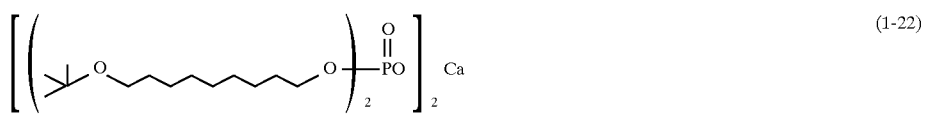
(1-22)
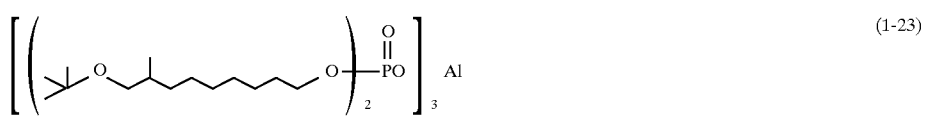
(1-23)
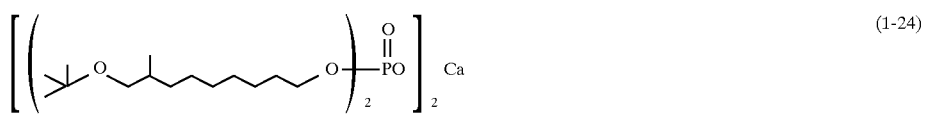
(1-24)
(1-25)
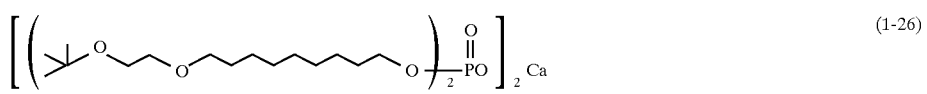
(1-26)
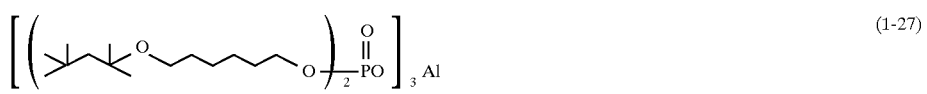
(1-27)
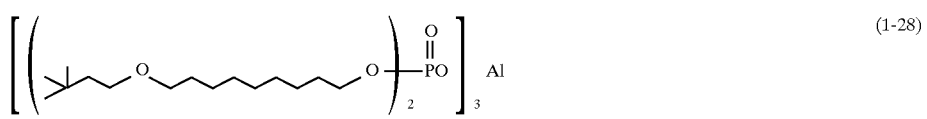
(1-28)
(1-29)
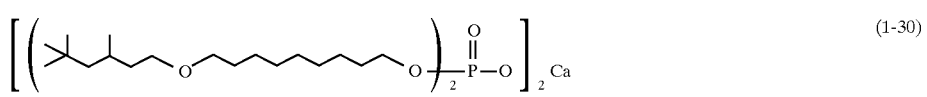
(1-30)
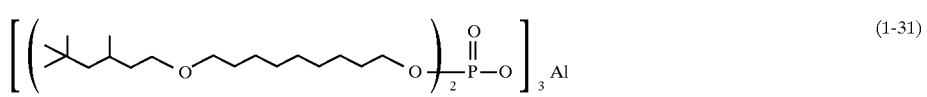
(1-31)

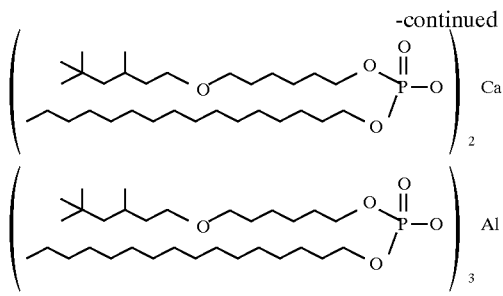

(1-32)

(1-33)

The polyvalent metal salts of phosphoric diesters according to the present invention are capable of gelling a variety of oily agents. Examples of such oily agents include oils and fats such as olive oil and tsubaki oil, hydrocarbons such as liquid paraffin, Vaseline and squalane; fatty acids such as lauric acid and stearic acid; higher alcohols such as stearyl alcohol and isostearyl alcohol; esters such as isopropyl myristate and isopropyl parmitate; silicone oils having a polysiloxane structure.

Among the polyvalent metal salts of phosphoric diesters according to the present invention, those in which at least one end of alkyls represented by $R^1$ or L' in formula (1) is $(CH_3)_3C$— have excellent performance in gelling silicone oils.

In formula (9) which represents the organo(poly)siloxane modified with a polyvalent metal salt of phosphoric diester (hereinafter referred to as "modified organo(poly)siloxane") according to the present invention, examples of $R^5$, which is a C2 to C20, preferably a C6 to C12 alkylene group, include ethylene, propylene, trimethylene, butylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, and the like. Of these, hexamethylene, heptamethylene, octamethylene, nonamethylene, undecamethylene and dodecamethylene are particularly preferred.

Examples of $R^6$, which is a C1 to C50, preferably a C1 to C10 linear or branched alkylene group which may be substituted by a hydroxy group, include methylene, ethylene, trimethylene, propylene, 1-methylpropylene, butylene, pentamethylene, 3-methylbutylene, 1,1-dimethylpropylene, hexamethylene, octamethylene, nonamethylene, decamethylene, undecamethylene, 2-hydroxyethylene, 2-hydroxybutylene and 2-hydroxyoctamethylene, among which methylene, propylene, butylene, pentamethylene, hexamethylene and octamethylene are particularly preferred.

p is a number from 0 to 200, preferably from 0 to 10, and more preferably from 0 to 5.

Examples of divalent or polyvalent metal atoms, represented by M, include alkaline earth metals and divalent or polyvalent transition metals. Examples of the alkaline earth metals include Mg, Ca and Ba. Examples of the divalent or polyvalent transition metals include Mn, Co, Al, Ni, Cu, V, Mo and Nb. Of these metal atoms, Ca, al and Fe are especially preferred.

Preferable examples of the alkyl groups represented by $R^7$ and $R^8$ in formula (9) and by $R^9$ and $R^{10}$ in formula (10) which stands for another structural unit of the present modified organo(poly)siloxane include C1 to C22 alkyl groups such as methyl, ethyl, propyl, isopropyl, butyl, hexyl, pentyl, t-butyl, octyl, tetradecyl, docosyl and octadecyl, and preferable examples of the alkoxy groups include C1 to C22 alkoxy groups such as methoxy, ethoxy, propoxy, pentyloxy, butoxy, 2-ethylbutoxy and 2-ethylhexyloxy.

The modified organo(poly)siloxanes according to the present invention are not particularly limited so long as they have the structural units represented by formulae (9) and (10). The manner of linking of the units is not particularly limited. The units (9) and (10) may form a linear linkage structure, a network structure, a cyclized structure, or a mixed structure of these. Moreover, units (9) and (10) may be linked at random or in block, respectively.

The most preferable modified organo(poly)siloxane according to the present invention are those having the structure of formula (11).

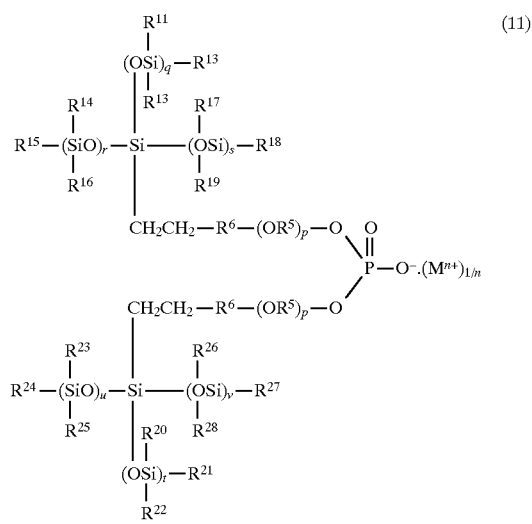

wherein $R^5$, $R^6$, p, M and n have the same meaning as defined hereinbefore, $R^{11}$ to $R^{28}$ each independently represent C1 to C22 alkyl or alkoxy, or phenyl, with the proviso that $R^{15}$ and $R^{24}$ may join together to be a divalent oxygen atom, with methyl being particularly preferred, and q, r, s, t, u and v each independently represent a number from 0 to 1000.

Preberable examples of the modified organo(poly)siloxanes represented by formula (11) according to the present invention include the following (11-a)–(11-m).

formula-1

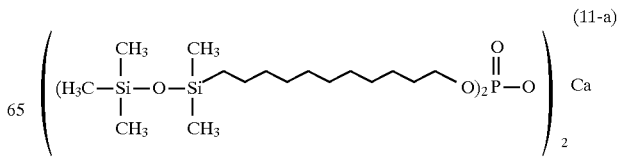

(11-a)

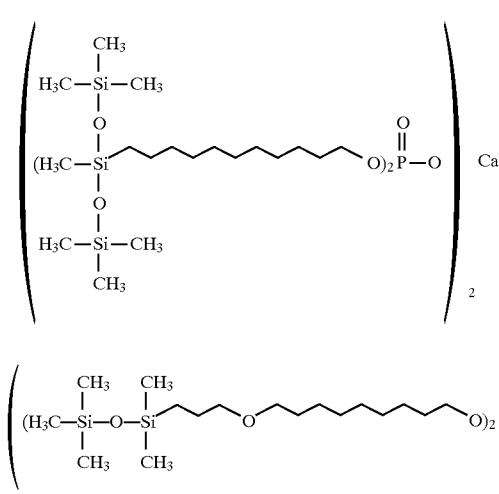
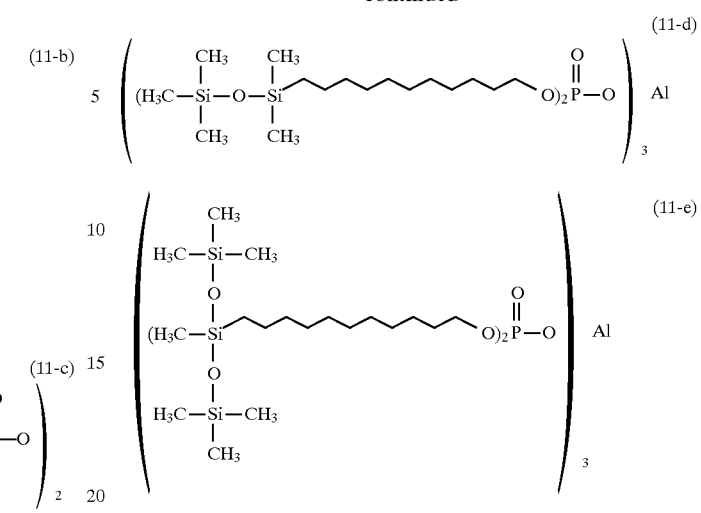
formula-2
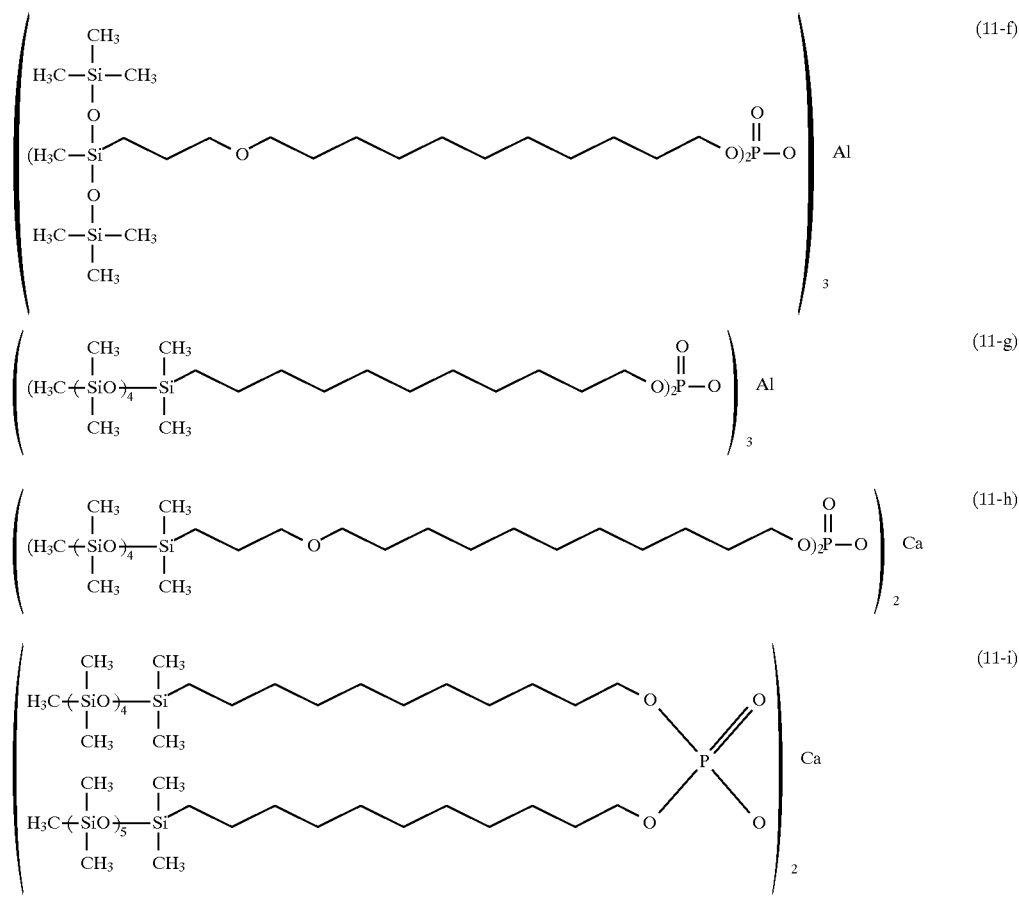

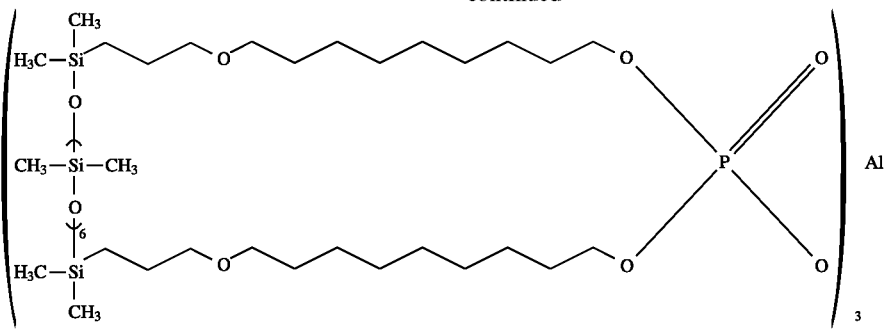
(11-j)

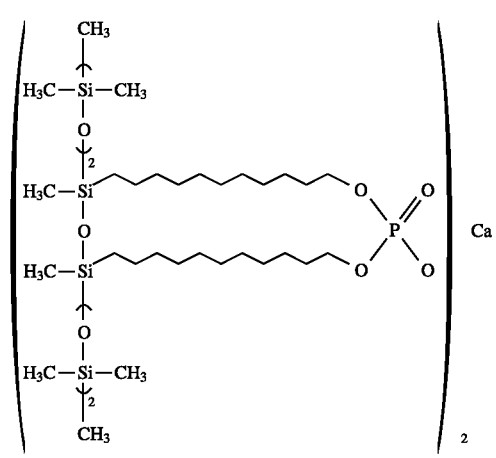
(11-k)

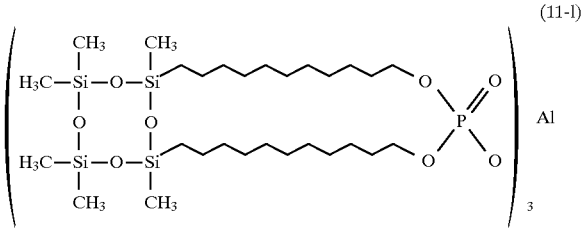
(11-l)

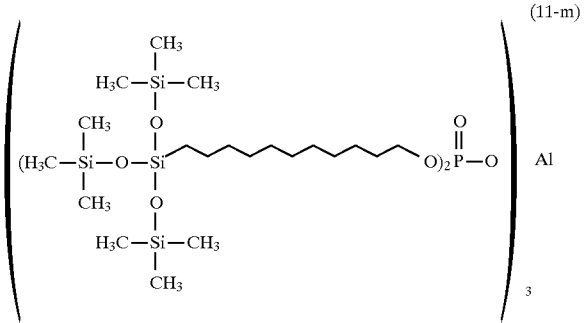
(11-m)

The modified organo(poly)siloxanes according to the present invention are prepared by reacting an organo(poly)siloxane having the following structural units (12) and (10):

$$-\underset{\underset{H}{|}}{\overset{\overset{R^7}{|}}{Si}}O- \qquad (12)$$

$$-\underset{\underset{R^{10}}{|}}{\overset{\overset{R^9}{|}}{Si}}-(O)_w- \qquad (10)$$

wherein $R^7$, $R^9$, $R^{10}$ and w have the same meaning as defined hereinbefore, with a polyvalent metal salt of phosphoric diester containing an unsaturated group represented by formula (13):

$$\begin{array}{c}CH_2=CH-R^6-(OR^5)_p-O\\ \phantom{CH_2=CH-R^6-(OR^5)_p-}\diagdown\phantom{O}\\ \phantom{CH_2=CH-R^6-(OR^5)_p-O}P-O^-.(M^{n+})_{1/n}\\ \phantom{CH_2=CH-R^6-(OR^5)_p-}\diagup\phantom{O}\\ CH_2=CH-R^6-(OR^5)_p-O\end{array} \qquad (13)$$

wherein $R^5$, $R^6$, p, M and n have the same meaning as defined hereinbefore.

The organo(poly)siloxanes having units represented by formulae (12) and (10), which are to be used in the present invention, are not particularly limited so long as they have these structural units of formulae (12) and (10). The manner of linking of the units is not particularly limited. The units (12) and (10) may form a linear linkage structure, a network structure, a cyclized structure, or a mixed structure of these. Moreover, units (12) and (10) may be linked at random or in block, respectively.

Preferable examples of these organo(poly)siloxanes are shown below.

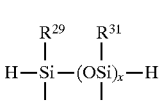

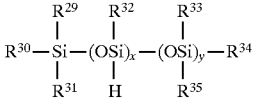

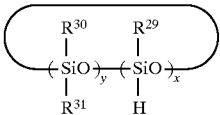

-continued

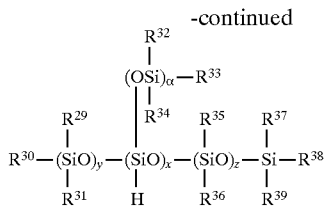

wherein
$R^{29}$ to $R^{39}$ each independently represent alkyl (preferably C1 to C22 alkyl), alkoxy (preferably C1 to C22 alkoxy) or phenyl, with methyl being particularly preferred, x, y, z and α each independently represent a number from 0 to 1000, with x being preferably from 1 to 10 and the others being preferably from 0 to 80.

Examples of these organo(poly)siloxanes include 1,3,5,7,9-pentamethyl cyclopentasiloxane, 1,3,5,7-tetramethyl cyclotetrasiloxane, 1,1,1,3,5,7,7,7-octamethyl tetrasiloxane, tris(trimethylsiloxy)silane, 1,1,3,3,5,5-hexamethyltrisiloxane, 1,1,1,3,5,5,5-heptamethyl trisiloxane, pentamethyl disiloxane, 1,1,3,3-tetramethyl disiloxane, triethylsilane, diethylmethylsilane, 1,3-diphenyl-1,3-dimethylsiloxane, diphenylmethylsilane, 1,1,1,3,3,5,5-heptamethyl trisiloxane, methyltris(dimethylsiloxy)silane, 1,1,3,3,5,5,7,7-octamethyl tetrasiloxane, phenyl dimethylsilane, triisopropylsilane, tri-n-octylsilane and triphenylsilane.

In the practice of the present invention, the above-described organo(poly)siloxanes to be used may be those prepared by a variety of conventional methods or may be commercial products obtainable from the market. Examples of the commercial products include TSF484, TSF483, XF40-A2606, XF40-A1629, XF40-A5149 and XF40-A2484 (all manufactured by Toshiba Silicone K.K.)

Furthermore, in the practice of the present invention, the polyvalent metal salts of a phosphoric diester containing an unsaturated group represented by formula (13) are prepared by any known methods. For example, they may be prepared in a following manner: First, a phosphorus oxyhalide and 2 to 4 fold mols, preferably 2 to 2.5 fold mols based on the amount of halide of an alcohol having an unsaturated bond at the terminal, represented by the formula $CH_2=CH—R^{26}—(OR^5)_p—OH$, wherein $R^5$, $R^6$ and p have the same meaning as defined hereinbefore, are allowed to react in a solvent such as tetrahydrofuran, diethylether, methylene chloride and toluene, in the presence of a catalyst such as triethylamine, tributylamine, and pyridine at −30° to −10° C. for 2 to 4 hours, then at 0° to 10° C. for 2 to 12 hours to obtain a corresponding phosphoric diester. Next, the obtained diester and 1/n to 10 fold equivalent (n has the same meaning as defined hereinbefore) based on the amount of diester of a salt of divalent or polyvalent metals such as $Ca(CH_3COO)_2$, $CaCl_2$, $CaBr_2$, $CaCO_3$, $Al_2(SO_4)_3$, $Al(CH_3COO)_3$, $AlCl_3$, $Al(NO_3)_3$, $BaCO_3$, $Fe(ClO_4)_3$, $Fe(NO_3)_3$, $FeCl_3$ and $Mn(VH_3COO)_2$ are allowed to react in a solvent mixture containing water and a solvent such as tetrahydrofuran, ethanol, methanol and butanol at 20° to 70° C., followed by purifying by recrystallization, washing and the like if necessary, to obtain a polyvalent metal salt of a phosphoric diester containing an unsaturated group represented by formula (13).

In the practice of the present invention, an organo(poly)siloxane having structural units (12) and (10) described hereinbefore and a formula (13) compound which is a polyvalent metal salt of a phosphoric diester containing an unsaturated group are reacted in a solvent such as toluene, hexane, chloroform, diisopropylether and tetrahydrofuran which is capable of dissolving the starting material and which has a volume of 1 to 100 fold on a weight basis of the total weight of the starting materials, at 20° to 100° C. for 1 to 10 hours.

In carrying out this reaction, it is preferred that a transition metal such as platinum, rhodium, nickel and palladium, a transition metal compound or a transition metal complex be added as a catalyst in an amount of $10^{-4}$ to $10^{-6}$ fold mols of the total amounts of the starting materials. The reaction ratio between the starting organo(poly)siloxane and the polyvalent metal salt of a phosphoric diester containing an unsaturated group is not particularly limited and may be determined in accordance with the ultimate denaturation degree of the target modified organo(poly)siloxane. For example, given that the number of SiH bonds in the starting organo(poly)siloxane is J, and if all the SiH bonds in the number of J are to be modified, not less than J/2 mols, preferably from J/2 to 5×J fold mols of a polyvalent metal salt of a phosphoric diester containing an unsaturated group based on the amount of organo(poly)siloxane are used.

After completion of the reaction, the catalyst is removed by filtration using activated carbon and the like, the solvent is evaporated, and subsequently, unreacted organo(poly)siloxanes or the like are discarded by acetone washing or the like, thereby obtaining an organo(poly)siloxane modified with polyvalent metal salt of a phosphoric diester according to the present invention.

The thus obtained polyvalent metal salts of phosphoric diesters and organo(poly)siloxanes modified with polyvalent metal salts of phosphoric diesters are useful as a gelling agent in various technical fields such as electric, electronics, automobiles, machines, medicines, cosmetics, fibers, papers, pulps, building materials, paints and in other technical fields so long as oil ingredients or silicone oils are utilized. In particular, application to the cosmetic field is preferable. When the compounds are incorporated into cosmetic compositions, it is preferred that the amounts be 0.01 to 20% by weight, particularly 0.3 to 6% by weight based on the total weight of the composition. Amounts less than 0.01% by weight cannot achieve satisfactory stability of the cosmetic compositions, and amounts exceeding 20% by weight render the composition system very viscous, resulting in poor quality of cosmetics with deteriorated extendibility, greasiness and sticky sensation.

The cosmetic compositions according to the present invention optionally contain polyether modified silicones, ordinary oils for cosmetics, humectants, intercellular lipids such as ceramide, UV absorbers, chelating agents, pH modifiers, preservatives, thickeners, colorants, pharmaceuticals, emulsifiers, detergent components and the like, besides silicone oils such as dimethylpolysiloxane, methylphenylpolysiloxane, octamethylcyclotetrasiloxane and decamethylcyclopentasiloxane, so long as the effects of the invention are not impeded.

The cosmetic compositions according to the present invention are prepared into apparently uniform gels by blending and stirring the above-described ingredients by conventional methods. Moreover, when components which constitute an emulsion phase or an aqueous phase are added, stable W/O or O/W emulsion cosmetic compositions can be obtained. When 10 to 40% by weight, preferably 15 to 30% by weight of powders are incorporated into the thus obtained gels or emulsions, foundations of an emulsion type or a cream type can be obtained. Examples of such powders include body pigments which are ordinarily employed in the manufacture of cosmetics, such as talc, mica, kaolin, and sericite; inorganic pigments such as titanium oxide, zinc oxide, iron oxide and ultramarine; pearling pigments of titanium-mica type; organic pigments such as Blue #404, Red #202 and Yellow #401. In the present invention, one or more of the above-described pigments are arbitrarily selected and used.

The cosmetic compositions according to the present invention encompass hair-care compositions such as hair styling compositions, shampoos, rinses and the like.

EXAMPLES

The present invention will be described in more detail by way of examples, which however, should not be construed as limiting the invention thereto.

Example 1

Preparation of a Calcium Salt of Phosphoric Diester (1-1)

(1) 350 g (3.00 mol) of 1,6-hexanediol, 50 g (1.25 mol) of sodium hydroxide and 1 liter of xylene were placed in a 3-liter four-neck flask equipped with a Dean-Stark trap, and heated to 100° C. while introducing nitrogen gas. Subsequently, 120 g (0.62 mol) of 2-ethylhexyl bromide was added dropwise thereto, and refluxed until water is no more discharged. After completion of the reaction, 1 liter of toluene was added for dilution, and washing was effected by the use of a diluted hydrochloric acid, water, saturated sodium bicarbonate water, water and saturated saline in this order, followed by drying over anhydrous magnesium sulfate. After filtration, the solvent was evaporated, and purification was conducted by distillation under reduced pressure to obtain 125 g of a monoether as a colorless oil.

A GLC analysis revealed a 97% purity. $^1$H-NMR at 200 MHz revealed proton signals of hydroxy at $\delta=1.5$, methine and methylene at $\delta=1.2–1.5$, 3.3, 3.35, 3.65, and methyl at $\delta=0.85–0.95$, which confirmed that a monoether compound was produced.

(2) 115 g (0.50 mol) of the monoether obtained in (1) above was placed in a 300-ml four-necked flask, and 24.0 g (0.167 mol) of phosphorus pentaoxide was added thereto under stirring while the temperature was maintained at a temperature not higher than 70° C. Stirring was continued for 4 hours while maintaining the reaction mixture at 75° to 85° C., then 10 ml of water was added thereto, and stirring was conducted for further 4 hours. Subsequently, the reaction mixture was transferred to a 1-liter autoclave, 15.3 g of sodium hydroxide was added as an aqueous 15% solution thereto, and the temperature was elevated to 145° C. while stirring and stirring was continued for 7 hours. The content was transferred to a 1-liter, three-neck flask equipped with a jacket, and 350 ml of an aqueous 10% sulfuric acid solution was added, the temperature was elevated to 60° C. and stirring was conducted for 1 hour. Thereafter, the flask was allowed to stand at room temperature, and the separated organic phase was washed with water. The solvent was evaporated and the residue was purified by distillation under reduced pressure to obtain 50 g of a phosphoric diester (2-1) represented by the following formula as a yellow oil.

$^{31}$P-NMR revealed a 99% purity and $^1$H-NMR (solvent: CDCl$_3$, TMS standard) at 200 MHz revealed proton signals of methine and methylene at $\delta=1.2–1.5$, 3.3, 3.35, 4.05, and methyl at $\delta=0.85–0.95$, which confirmed that a phosphoric diester was produced.

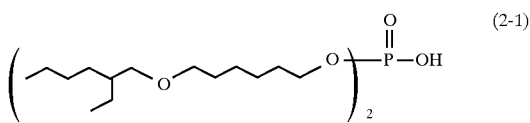

(2-1)

(3) 50 g of the thus obtained phosphoric diester (2-1) was added with 100 ml of ethanol, 16 g of calcium acetate and 100 ml of water, and stirred at 60 for 2 hours. After cooling down to room temperature, 200 ml of hexane was added for a phase separation. The organic phase was washed with water, the solvent was evaporated, and acetone was added for reprecipitation. 43 g of phosphoric diester calcium salt (1-1) was obtained as a white solid.

$^{31}$P-NMR revealed a 99% purity and $^1$H-NMR at 200 MHz revealed proton signals of methine and methylene at $\delta=1.2–1.5$, 3.3, 3.35, 3.85, and methyl at $\delta=0.85–0.95$, which confirmed that a calcium salt of phosphoric diester was produced.

Example 2

Preparation of a Calcium Salt of Phosphoric Diester (1-3)

(1) 500 g (3.04 mol) of 1,9-nonanediol, 50 g (1.25 mol) of sodium hydroxide and 1 liter of xylene were placed in a 3-liter four-neck flask equipped with a Dean-Stark trap, and heated to 100° C. while introducing nitrogen gas. Subsequently, 120 g (0.62 mol) of 2-ethylhexyl bromide was added dropwise thereto, and refluxed until water is no more discharged. After completion of the reaction, 1 liter of toluene was added for dilution, and the crystals precipitated were removed by filtration, and the mother liquor was washed with a diluted hydrochloric acid, water, saturated sodium bicarbonate water, water and saturated saline in this order, followed by drying over anhydrous magnesium sulfate. After filtration, the solvent was evaporated, and purification was conducted by distillation under reduced pressure to obtain 135 g of a monoether as a colorless oil.

A GLC analysis revealed a 99% purity. $^1$H-NMR at 200 MHz revealed proton signals of hydroxy at $\delta=1.5$, methine and methylene at $\delta=1.2–1.6$, 3.3, 3.35, 3.65, and methyl at $\delta=0.85–0.95$, which confirmed that a monoether compound was produced.

(2) 150 g (0.515 mol) of the monoether obtained in (1) above was placed in a 300-ml four-neck flask, and 25.0 g (0.172 mol) of phosphorus pentaoxide was added thereto under stirring while maintaining the temperature not higher than 70° C. Stirring was continued for 4 hours while maintaining the reaction temperature at 75° to 85° C., then 17.5 ml of water was added thereto, and stirring was conducted for further 4 hours. Subsequently, the reaction mixture was transferred to a 1-liter autoclave, 10.5 g of sodium hydroxide was added as an aqueous 15% solution thereto, and the temperature was elevated to 145° C. while stirring and stirring was continued for 7 hours. The content was transferred to a 1-liter, three-neck flask equipped with a jacket, and 350 ml of an aqueous 10% sulfuric acid solution was added, the temperature was elevated to 60° C. and stirring was conducted for 1 hour. Thereafter, the flask was allowed to stand at room temperature, and the separated organic phase was washed with water. The resulting product was added with 100 ml of ethanol, 20 g of calcium acetate and 100 ml of water, and stirred at 60° C. for 2 hours, followed by cooling down to room temperature. 200 ml of hexane was added for a phase separation. The organic phase was washed with water, the solvent was evaporated, and acetone was added for reprecipitation. The solid precipitated was collected by filtration, dried to obtain 62 g of a calcium salt of phosphoric diester (1-3) as a white solid.

Example 3

Preparation of a Calcium Salt of Phosphoric Diester (1-5)

(1) 500 g (2.81 mol) of 2-(2-ethylhexyloxy)ethanol and 500 g of thionyl chloride were placed in a 2-liter four-neck flask and refluxed with heat for 2 hours. Subsequently, a distillation under reduced pressure was conducted to obtain 510 g of 2-(2-ethylhexyloxy)ethylchloride as a colorless oil.

(2) 500 g (3.04 mol) of 1,9-nonanediol, 50 g (1.25 mol) of sodium hydroxide and 1 liter of xylene were placed in a 3-liter four-neck flask equipped with a Dean-Stark trap, and heated to 100° C. while introducing nitrogen gas. Subsequently, 120 g (0.62 mol) of 2-(2-ethylhexyloxy) ethylchloride was added dropwise thereto, and refluxed until water is no more discharged. After completion of the reaction, 1 liter of toluene was added for dilution, and the crystals precipitated were removed by filtration, and the mother liquor was washed with a diluted hydrochloric acid, water, saturated sodium bicarbonate water, water and saturated saline in this order, followed by drying over anhydrous magnesium sulfate. After filtration, the solvent was evaporated, and purification was conducted by distillation under reduced pressure to obtain 140 g of a monoether as a colorless oil.

A GLC analysis revealed a 98% purity. $^1$H-NMR at 200 MHz revealed proton signals of methine and methylene at !!1.2–1.5, 3.35, 3.45, 3.55 and 3.65, and methyl at $\delta$=0.85–0.9, which confirmed that a monoether compound was produced.

(3) 140 g (0.507 mol) of the monoether obtained in (1) above was placed in a 300-ml four-neck flask, and 25.0 g (0.172 mol) of phosphorus pentaoxide was added thereto under stirring while maintaining the temperature not higher than 70° C. Stirring was continued for 4 hours while maintaining the reaction temperature at 75° to 85° C., then 17.5 ml of water was added thereto, and stirring was conducted for further 4 hours. Subsequently, the reaction mixture was transferred to a 1-liter autoclave, 10.5 g of sodium hydroxide was added as an aqueous 15% solution thereto, and the temperature was elevated to 145° C. while stirring and stirring was continued for 7 hours. The content was transferred to a 1-liter, three-neck flask equipped with a jacket, and 350 ml of an aqueous 10% sulfuric acid solution was added, the temperature was elevated to 60° C. and stirring was conducted for 1 hour. Thereafter, the flask was cooled down to room temperature, and ether was added for a phase separation. The organic phase separated was washed with water, and the solvent was evaporated. The resulting product was added with 100 ml of ethanol, 20 g of calcium acetate and 100 ml of water, and stirred at 60° C. for 2 hours, followed by cooling down to room temperature. 300 ml of ether was added for a phase separation. The organic phase was washed with water, the solvent was evaporated, and acetone was added for reprecipitation. The solid precipitated was collected by filtration, dried to obtain 60 g of a calcium salt of phosphoric diester (1-5) as a white solid.

$^{31}$P-NMR revealed a 99% purity and $^1$H-NMR at 200 MHz revealed proton signals of methine and methylene at $\delta$=1.2–1.6, 3.35, 3.45, 3.55 and 3.85, and methyl at $\delta$=0.85–0.9, which confirmed that a calcium salt of phosphoric diester was produced.

Example 4

Preparation of an Aluminum Salt of Phosphoric Diester (1-9)

(1) 500 g (3.04 mol) of 1,9-nonanediol, 50 g (1.25 mol) of sodium hydroxide and 1 liter of xylene were placed in a 3-liter four-neck flask equipped with a Dean-Stark trap, and heated to 100° C. while introducing nitrogen gas. Subsequently, 120 g (0.62 mol) of 2-ethylhexyl bromide was added dropwise thereto, and refluxed until water is no more discharged. After completion of the reaction, 1 liter of toluene was added for dilution, and the crystals precipitated were removed by filtration, and the mother liquor was washed with a diluted hydrochloric acid, water, saturated sodium bicarbonate water, water and saturated saline in this order, followed by drying over anhydrous magnesium sulfate. After filtration, the solvent was evaporated, and purification was conducted by distillation under reduced pressure to obtain 135 g of a monoether as a colorless oil.

A GLC analysis revealed a 99% purity. $^1$H-NMR at 200 MHz revealed proton signals of hydroxy at $\delta$=1.5, methine and methylene at $\delta$=1.2–1.6, 3.3, 3.35 and 3.65, and methyl at $\delta$=0.85–0.95, which confirmed that a monoether compound was produced.

(2) 150 g (0.515 mol) of the monoether was placed in a 300-ml four-neck flask, and 25.0 g (0.172 mol) of phosphorus pentaoxide was added thereto under stirring while maintaining the temperature not higher than 70° C. Stirring was continued for 4 hours while maintaining the reaction temperature at 75° to 85° C., then 17.5 ml of water was added thereto, and stirring was conducted for further 4 hours. Subsequently, the reaction mixture was transferred to a 1-liter autoclave, 10.5 g of sodium hydroxide was added as an aqueous 15% solution thereto, and the temperature was elevated to 145° C. while stirring and stirring was continued for 7 hours. The content was transferred to a 1-liter, three-neck flask equipped with a jacket, and 350 ml of an aqueous 10% sulfuric acid solution was added, the temperature was elevated to 60° C. and stirring was conducted for 1 hour. Thereafter, the flask was allowed to stand at room temperature, and the organic phase separated was further washed. The resulting material was added with 100 ml of ethanol, 30 mg of aluminum acetate and 100 ml of water, and stirring was effected at 60° C. for 2 hours, followed by cooling down to room temperature. The solid precipitated was collected by filtration, dried to obtain 70 g of an aluminum salt of phosphoric diester (1-9) as a white solid.

$^{31}$P-NMR revealed a 99% purity and $^1$H-NMR at 200 MHz revealed proton signals of methine and methylene at $\delta$=1.2–1.6, 3.3, 3.35, and 3.8, and methyl at $\delta$=0.85–0.9, which confirmed that an aluminum salt of phosphoric diester was produced.

Example 5

Preparation of an Aluminum Salt of Phosphoric Diester (1-21)

(1) 200 g (2.7 mol) of tert-butanol, 100 g (0.625 mol) of 1,9-nonanediol and 2 g of sulfuric aid were placed in a 500 ml round bottomed flask, and refluxed with heat for 5 hours, followed by neutralizing with an aqueous sodium hydroxide solution. After unreacted tert-butanol was evaporated, hexane was added and stirred. The diol insoluble in hexane was discarded by filtration. The hexane layer was washed with water, and dried with anhydrous sodium sulfate. After filtration, the solvent was evaporated and the residue was purified by silica gel column chromatography (hexane/chloroform) to obtain 35 g of 9-tert-butoxy-1-nonanol as a colorless oil.

A GLC analysis revealed a purity of not less than 99%. $^1$H-NMR(solvent: CDCl$_3$, TMS standard) revealed proton signals of methyl originated from tert-butyl at $\delta$=1.2, methylene at $\delta$=1.3, 1.5–1.6, 3.35 and 3.65, respectively, which confirmed that a monoether compound was produced.

(2) 5.0 g (0.033 mol) of phosphorus oxychloride was dissolved in THF, and cooled below −50° C. while introducing nitrogen gas. 15 g (0.069 mol) of monoether obtained in step (1) and a solution of 7.0 g (0.069 mol) of triethylamine in THF were added dropwise thereto. After completion of the addition, the mixture was heated to 0!! and stirred overnight. 1.26 g of water was added dropwise, and stirred for a while, and then the precipitated triethylamine hydrochloride was removed by filtration. The solvent was evaporated to quantitatively obtain a triethylamine salt of phosphoric diester as a yellow oil, which was confirmed by $^{31}$P-NMR.

(3) 4 g of the triethylamine salt of phosphoric diester obtained in step (2) was dispersed in 1.5N hydrochloric acid, and stirred for 3 hours at 40° to 50° C. Extraction was performed with hexane. After washing with water, the solvent was evaporated to obtain a phosphoric diester in colorless oil. The thus obtained phosphoric diester was dissolved in ethanol, to which 4 g of aluminum acetate/ethanol/water was added and stirred at 50° C. for 30 minutes. Two fold in amount of water was added thereto, then the mixture was cooled to room temperature, and the precipitated solid was collected by filtration, which was washed with water, ethanol and acetone, followed by drying to obtain 2.5 g of aluminum salt of phosphoric diester (1-21) as a white solid.

$^{31}$P-NMR revealed a purity of 99% or more, and $^1$H-NMR at 200 MHz revealed proton signals of methyl at δ=1.2, and methylene at δ=1.3, 1.5, 1.68, 3.3 and 3.98, which confirmed that an aluminum salt of phosphoric diester was produced.

Example 6

Preparation of Aluminum Salt of Phosphoric Diester (1-23)

(1) In place of 1,9-nonanediol in Example 5, 2-methyl-1,8-octanediol was used to carry out a synthesis in a similar manner as described in Example 5.

$^{31}$P-NMR revealed a purity of 99% or more, and $^1$H-NMR (solvent: CdCl$_3$, TMS standard) at 200 MHz revealed proton signals of methyl at δ=0.88 and 1.2, and methylene and methine at δ=1.3–1.5, 1.7, 3.3 and 3.98, which confirmed that an aluminum salt of phosphoric diester (1-23) was produced.

Example 7

Preparation of Aluminum Salt of Phosphoric Diester (1-28)

(1) 10 g (0.10 mol) of 3,3-dimethyl-1-butanol and 8 g (0.10 mol) of pyridine were dissolved in benzene, to which 12 g of thionyl chloride in benzene was added dropwise on ice, and refluxed at 80° C. for 5 hours. 100 ml of water was added thereto while cooled on ice, followed by drying over anhydrous magnesium sulfate. After filtration, the solvent was evaporated, and the obtained 5 g of 1-chloro-3,3-dimethylbutane in pale-yellow oil was dissolved in toluene. 25 g (0.156 mol) of 1,9-nonanediol was dissolved in toluene, to which 3.2 g (0.08 mol) of sodium hydroxide was added and then azeotropically dehydrated for 1 hour by the use of a Dean-Stark trap. 1 chloro-3,3-dimethylbutane in toluene was added dropwise, and refluxed with heat for 5 hours, then allowed to cool down to room temperature. Two-fold in amount of hexane was added and insoluble matter was removed by filtration. the hexane/toluene phase was washed with water and concentrated to obtain a mixture of monoether and diether in a proportion of 60:40 as a yellow oil. The oil was purified by silica gel column chromatography (chloroform) to obtain 5 g of monoether in a pale-yellow oil.

A GLC analysis revealed a 95% purity. $^1$H-NMR (solvent: CDCl$_3$, TMS standard) revealed proton signals of methyl originated from tert-butyl at δ=0.9, methylene at δ=1.32, 1.55–1.7, 3.45 and 3.65, respectively, which confirmed that a monoether compound was produced.

(2) 0.91 g (0.0059 mol) of phosphorus oxychloride was dissolved in THF, and cooled below 0° C. while introducing nitrogen gas. 3.7 g (0.015 mol) of monoether obtained in step (1) and 1.2 g (0.012 mol) of triethylamine in THF were added dropwise thereto. After completion of the addition, the mixture was stirred for 18 hours. 200 mg of water in THF was added dropwise, stirred for a while, and then dispersed in 2N hydrochloric acid, followed by stirring for 2 hours. Extraction was performed with hexane, and after washing the extract, the residue from which the solvent was evaporated was dissolved in ethanol. 5.0 g of aluminum/ethanol/water was added and stirred at 50° C. for 1.5 hours. Two-fold in amount of water was added, and cooled to room temperature, then the precipitated solid was collected by filtration. The collected material was washed with water, ethanol and acetone, and dried to obtain 1.5 g of an aluminum salt of phosphoric diester (1-28) as a pale-yellow solid.

$^{31}$P-NMR revealed a purity of 99% or more, and $^1$H-NMR (solvent CDCl$_3$, TMS standard) at 200 MHz revealed proton signals of methyl at δ=0.9, and methylene at δ=1.32, 1.55–1.7, 3.45 and 4.0, which confirmed that an aluminum salt of phosphoric diester was produced.

Example 8

Polyvalent metal salts of phosphoric diester were evaluated with respect to the gel-forming performance on oil.

In detail, 1 g of a compound was placed in a sample tube, and 19 g of oil was added. The content was mixed for about 3 minutes by the use of an ultrasonic mixer for uniform dispersion or solution. The obtained uniform mixture was allowed to stand for a day and night, and thereafter, the status of the mixture was visually checked and evaluated in accordance with the following criteria:

A: Transparent and viscous gel.

B: Gel of low viscosity.

C: Gel formed with oozing of oil.

D: Insoluble.

The results are shown in Table 1.

TABLE 1

| | Compounds | | | | |
|---|---|---|---|---|---|
| | Compounds of invention | | | | Comparative[1] |
| Oils | 1-1 | 1-3 | 1-5 | 1-9 | product |
| Light-liquid paraffin | A | A | A | A | A[2] |
| Isopropyl palmitate | B | A | A | A | D |
| 1-Isostearoyl-3-myristoyl glycerol | B | B | B | B | D |

1): [ 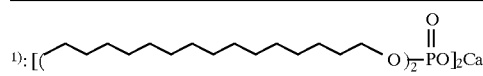

2): Hard gel lacking transparency

Example 9

In a similar manner to Example 8, polyvalent metal salts of phosphoric diester were evaluated with respect to the gel-forming performance on oil.

The test was performed as follows: 2 wt % of compounds were added to the sample oils, respectively, and allow to stand at room temperature for 1 to 3 days. Thereafter, the system was stirred with heat at 40° to 80° C. for 1 to 4 hours for a uniform dispersion or solution. Subsequently, the uniform system was further allowed to stand for a day and night, and thereafter the condition was visually checked in accordance with the following criteria:

A: Oils are gelled.
B: Oils are gelled with remaining insoluble matters.
C: Separation of oil and gel.
D: Gel is not formed.

TABLE 2

| | Compounds | | |
|---|---|---|---|
| | Compounds of invention | | |
| Oils | 1-21 | 1-23 | 1-28 |
| Liquid paraffin | B | C | A |
| Neopentylglycol dicaprylate | A | C | A |
| silicone oil[1] | A | A | A |

[1]: Octamethyl cyclotetrasiloxane (LS-8620, product of Shin'etsu Kagaku Kogyo k.K.)

Example 10

The sun-screening gel of the following formulation was prepared by the process described below.
(Formulation)

| 1) Compound (1-1) in Example 1 | 4 wt % |
|---|---|
| 2) Squalane | balance |
| 3) Methylphenyl polysiloxane | 5 |
| 4) Isooctyl p-dimethylaminobenzoate | 2 |
| 5) Perfume | suitable amount |

(Process)
Components (1) to (4) were heated and uniformly dissolved with a disperser. Component (5) was added thereto and uniformly mixed with a disperser to obtain a sun-screen gel.

No dripping or running down of liquid from fingers was occurred during use of the obtained gel composition. The composition was free of stickiness, and was excellent in sensation during use, too.

Example 11

The sun-screening cream of the following formulation was prepared by the process described below.
(Formulation)

| 1) Compound (1-3) in Example 2 | 4 wt % |
|---|---|
| 2) Isopropyl palmitate | balance |
| 3) Dimethyl polysiloxane (6 cs) | 5 |
| 4) Octyl methoxycinnamate | 3 |
| 5) Titanium oxide | 5 |
| 6) Perfume | suitable amount |

(Process)
Components (1) to (4) were heated and uniformly dissolved with a disperser. Component (5) and (6) were added thereto and uniformly mixed with a disperser to obtain a sun-screen cream.

The obtained cream was excellent in the stability of pigment dispersion and was excellent in sensation during use.

Example 12

The oil-based detergent of the following formulation was prepared by the process described below.
(Formulation)

| 1) Compound (1-5) in Example 3 | 3 wt % |
|---|---|
| 2) Glyceryl POE (20) triisostearate | 10 |
| 3) Squalane | 40 |
| 4) Isooctyl palmitate | 47 |

(Process)
Components (1) to (4) were heated and uniformly dissolved with a disperser.

The obtained composition was stable and excellent in sensation during use. No dripping or running down of liquid from fingers was occurred during use of the obtained composition.

Example 13

The creamy W/O-type foundation of the following formulation was prepared by the process described below.
(Formulation)

| 1) | Compound (1-9) in Example 4 | 10 wt % |
|---|---|---|
| 2) | Dimethylpolysiloxane (6 cs) | 5 |
| 3) | Squalane | 40 |
| 4) | Glycerol | 2 |
| 5) | Purified water | balance |
| 6) | Pigment | |
| | Sericite | 6 |
| | Titanium oxide | 8 |
| | Iron oxide | 12 |
| 7) | Nylon powder | 5 |
| 8) | Dimethylpolysiloxane/polyoxyalkylene copolymer | 1 |

(Process)
Components (1) to (3) and (8) were heated and uniformly dissolved with a disperser, to which components (6) and (7) were dissolved and dispersed with a disperser. Components (4) and (5) were added thereto while stirring for emulsification to obtain a foundation.

The obtained composition had excellent dispersion stability of pigments and was also excellent in sensation during use. Moreover, no dripping or running down of liquid from fingers was occurred during use of the composition.

Example 14

The creamy W/O-type foundation of the following formulation was prepared by the process described below.
(Formulation)

| 1) | Compound (1-21) in Example 5 | 10 wt % |
|---|---|---|
| 2) | Dimethylpolysiloxane (6 cs) | 5 |
| 3) | Squalane | 40 |
| 4) | Glycerol | 2 |
| 5) | Purified water | balance |
| 6) | Pigment | |
| | Sericite | 6 |
| | Titanium oxide | 8 |
| | Iron oxide | 12 |
| 7) | Nylon powder | 5 |
| 8) | Dimethylpolysiloxane/polyoxyalkylene copolymer | 1 |

(Process)
Components (1) to (3) and (8) were heated and uniformly dissolved with a disperser, to which components (6) and (7) were dissolved and dispersed with a disperser. Components (4) and (5) were added thereto while stirring for emulsification to obtain a foundation.

The obtained composition had excellent dispersion stability of pigments and was also excellent in sensation during use. Moreover, no dripping or running down of liquid from fingers was occurred during use of the composition.

Example 15

The creamy W/O-type foundation of the following formulation was prepared by the process described below.

(Formulation)

| | | |
|---|---|---|
| 1) | Compound (1-23) in Example 6 | 10 wt % |
| 2) | Dimethylpolysiloxane (6 cs) | 5 |
| 3) | Squalane | 40 |
| 4) | Glycerol | 2 |
| 5) | Purified water | balance |
| 6) | Pigment | |
| | Sericite | 6 |
| | Titanium oxide | 8 |
| | Iron oxide | 12 |
| 7) | Nylon powder | 5 |
| 8) | Dimethylpolysiloxane/polyoxyalkylene copolymer | 1 |

(Process)

Components (1) to (3) and (8) were heated and uniformly dissolved with a disperser, to which components (6) and (7) were dissolved and dispersed with a disperser. Components (4) and (5) were added thereto while stirring for emulsification to obtain a foundation.

The obtained composition had excellent dispersion stability of pigments and w as also excellent in sensation during use. Moreover, no dripping or running down of liquid from fingers was occurred during use of the composition.

Example 16

The creamy W/O-type foundation of the following formulation was prepared by the process described below.

(Formulation)

| | | |
|---|---|---|
| 1) | Compound (1-28) in Example 7 | 10 wt % |
| 2) | Dimethylpolysiloxane (6 cs) | 5 |
| 3) | Squalane | 40 |
| 4) | Glycerol | 2 |
| 5) | Purified water | balance |
| 6) | Pigment | |
| | Sericite | 6 |
| | Titanium oxide | 8 |
| | Iron oxide | 12 |
| 7) | Nylon powder | 5 |
| 8) | Dimethylpolysiloxane/polyoxyalkylene copolymer | 1 |

(Process)

Components (1) to (3) and (8) were heated and uniformly dissolved with a disperser, to which components (6) and (7) were dissolved and dispersed with a disperser. Components (4) and (5) were added thereto while stirring for emulsification to obtain a foundation.

The obtained composition had excellent dispersion stability of pigments and was also excellent in sensation during use. Moreover, no dripping or running down of liquid from fingers was occurred during use of the composition.

Example 17

Preparation of Compound (a) of the Present Invention

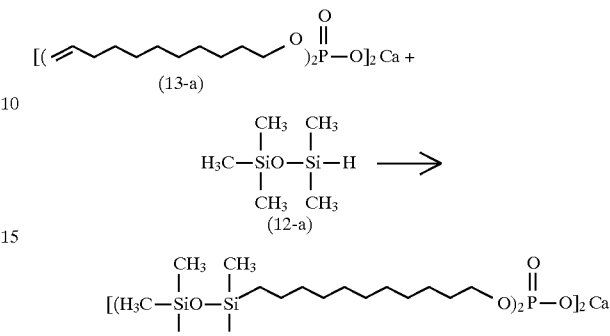

15 g of compound (13-a) was dissolved in 500 g of toluene, to which a solution of 11 g of compound (12-a) (product of Shin'estu Kagaku Kogyo K.K.) in 30 g of toluene was added. The resulting solution was added with chloroplatinic acid (in isopropyl alcohol, 30 microliters of 1% solution) and aged at 70° C. for 8 hours. After completion of the reaction, 100 g of methanol and 1 g of activated carbon were added thereto and stirred at 30° C. for 1 hour. Subsequently, the activated carbon was filtered off and the solvent was distilled off under reduced pressure. The residue was added with 100 g of chloroform for dissolving the product, and thereafter, 500 g of acetone was added and the solid deposited was filtered to obtain 23 g of the invention compound (a).

IR(KBr): Si—O—Si, 1070 cm$^{-1}$
$^1$H-NMR (CDCl$_3$):
 −0.1 ppm Si—CH$_3$, 0.4 ppm Si—CH$_2$, 1.2 ppm —CH$_2$—,
 1.6 ppm —(C$\underline{H}_2$)—CH$_2$O—P, 3.8 ppm —CH$_2$—C$\underline{H}_2$O—P
$^{31}$P—NMR(CDCl$_3$):
 −1.72 ppm

Example 18

Preparation of Compound (b) of the Present Invention

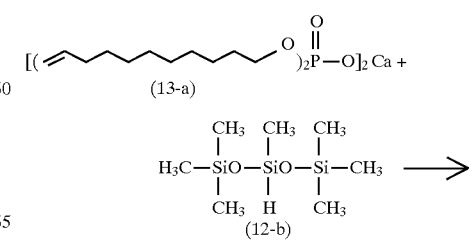

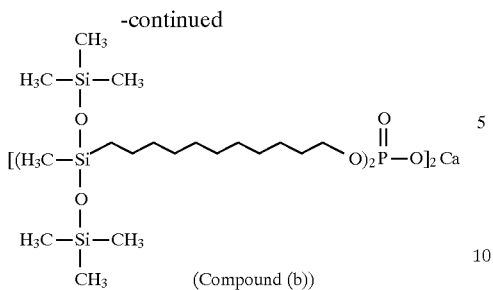

(Compound (b))

10 g of compound (13-a) was dissolved in 400 g of toluene, to which a solution of 11 g of compound (12-b) (product of Shin'estu Kagaku Kogyo K.K.) in 30 g of toluene was added. The resulting solution was added with chloroplatinic acid (in isopropyl alcohol, 30 microliters of 1% solution) and aged at 70° C. for 8 hours. After completion of the reaction, 100 g of methanol and 1 g of activated carbon were added thereto and stirred at 30° C. for 1 hour. Subsequently, the activated carbon was filtered off and the solvent was distilled off under reduced pressure. The residue was added with 100 g of chloroform for dissolving the product, and thereafter, 450 g of acetone was added and the solid deposited was filtered to obtain 20 g of the invention compound (b).

IR(KBr): Si—O—Si, 1060 cm$^{-1}$
$^1$H—NMR (CDCl$_3$):
  −0.1, −0.2 ppm Si—CH$_3$, 0.4 ppm Si—CH$_2$, 1.2 ppm —CH$_2$—, 1.5 ppm —(C$\underline{H}_2$)—CH$_2$O—P, 3.8 ppm —CH$_2$—C$\underline{H}_2$O—P
$^{31}$P—NMR(CDCl$_3$):
  −1.74 ppm —OPOCa$_{1/2}$
‖
O

Example 19

Preparation of Compound (c) of the Present Invention

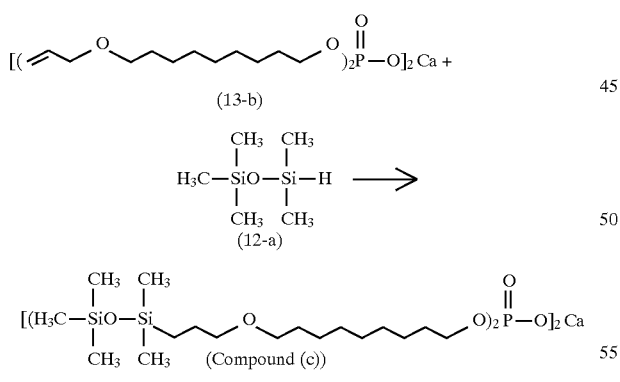

(Compound (c))

10 g of compound (13-b) was dissolved in 300 g of toluene, to which a solution of 7 g of compound (12-a) (product of Shin'estu Kagaku Kogyo K.K.) in 40 g of toluene was added. The resulting solution was added with chloroplatinic acid (in isopropyl alcohol, 30 microliters of 1% solution) and aged at 70° C. for 8 hours. After completion of the reaction, 100 g of methanol and 1 g of activated carbon were added thereto and stirred at 30° C. for 1 hour. Subsequently, the activated carbon was filtered off and the solvent was distilled off under reduced pressure. The residue was added with 100 g of chloroform for dissolving the product, and thereafter, 550 g of acetone was added and the solid deposited was filtered to obtain 15 g of the invention compound (c).

IR(KBr): Si—O—Si, 1057 cm$^{-1}$
$^1$H-NMR (CDCl$_3$):
  −0.1 ppm Si—CH$_3$, 0.4 ppm Si—CH$_2$, 1.2 ppm —CH$_2$—, 1.5 ppm —(C$\underline{H}_2$)—CH$_2$O—P, —(C$\underline{H}_2$)—C$\underline{H}_2$—O, 3.3 ppm —CH$_2$—O—CH$_2$—, 3.8 ppm —CH$_2$—C$\underline{H}_2$O—P
$^{31}$P—NMR(CDCl$_3$):
  −1.74 ppm

—OPOCa$_{1/2}$

Example 20

Preparation of Compound (d) of the Present Invention

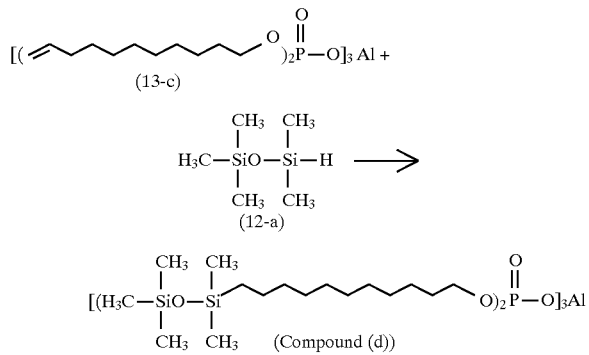

(Compound (d))

8.0 g of compound (13-c) was dissolved in 250 g of toluene, to which a solution of 6.5 g of compound (12-a) (product of Shin'estu Kagaku Kogyo K.K.) in 20 g of toluene was added. The resulting solution was added with chloroplatinic acid (in isopropyl alcohol, 30 microliters of 1% solution) and aged at 70° C. for 7 hours. After completion of the reaction, 100 g of methanol and 0.5 g of activated carbon were added thereto and stirred at 30° C. for 1 hour. Subsequently, the activated carbon was filtered off and the solvent was distilled off under reduced pressure. The residue was added with 100 g of chloroform for dissolving the product, and thereafter, 500 g of acetone was added and the solid deposited was filtered to obtain 13 g of the invention compound (d).

IR(KBr): Si—O—Si, 1047 cm$^{-1}$
$^1$H-NMR (CDCl$_3$ + CD$_3$OD):
  −0.1 ppm Si—CH$_3$, 0.45 ppm Si—CH$_2$, 1.23 ppm —CH$_2$—, 1.5 ppm P—O—CH$_2$—C$\underline{H}_2$, 3.9 ppm P—O—CH$_2$
$^{31}$P—NMR(CDCl$_3$ + CD$_3$OD):
  −14.8 ppm

OPOAl$_{1/3}$

Example 21

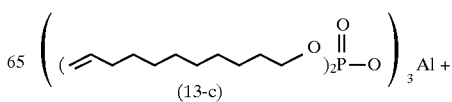

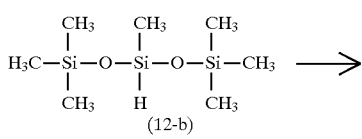
(12-b)

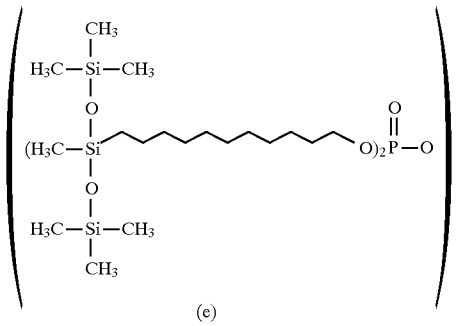
(e)

7 g of compound (13-c) was dissolved in 150 g of toluene, to which a solution of 7.8 g of compound (12-b) (product of Shin'estu Kagaku Kogyo K.K.) in 10 g of toluene was added. The resulting solution was added with chloroplatinic acid (in isopropyl alcohol) and aged at 70° C. for 7 hours. After completion of the reaction, 100 g of ethanol and 0.5 g of activated carbon were added thereto and stirred at 30° C. for 1 hour. Subsequently, the activated carbon was filtered off and the solvent was distilled off under reduced pressure. The residue was added with 100 g of chloroform for dissolving the product, and thereafter, 400 g of acetone was added and the solid deposited was filtered to obtain 13.8 g of the invention compound (e).

IR (KBr): Si—O—Si, 1020 cm$^{-1}$
$^1$H-NMR (CDCl$_3$):
 −0.1 ppm —CH$_2$—Si—$\underline{CH_3}$
 0 ppm —O—Si—$\underline{CH_3}$
 0.40 ppm —$\underline{CH_2}$—Si
 1.21 ppm —$\underline{CH_2}$—
 1.49 ppm —($\underline{CH_2}$)—CH$_2$—O—P
 3.90 ppm —$\underline{CH_2}$—O—P
 $^{31}$P-NMR (CDCl$_3$):
 −14.74 ppm

Example 22

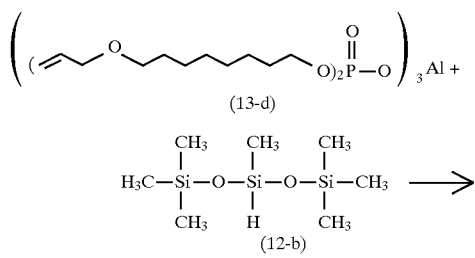
(13-d)

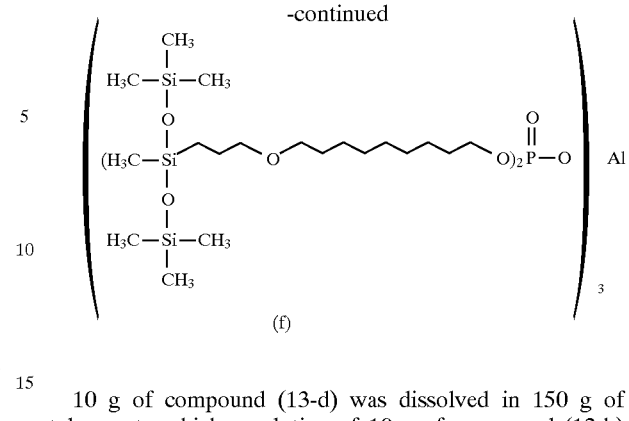
(f)

10 g of compound (13-d) was dissolved in 150 g of toluene, to which a solution of 10 g of compound (12-b) (product of Shin'estu Kagaku Kogyo K.K.) in 10 g of toluene was added. The resulting solution was added with chloroplatinic acid (in isopropyl alcohol) and aged at 70° C. for 7 hours. After completion of the reaction, 100 g of ethanol and 0.5 g of activated carbon were added thereto and stirred at 30° C. for 1 hour. Subsequently, the activated carbon was filtered off and the solvent was distilled off under reduced pressure. The residue was added with 50 g of chloroform for dissolving the product, and thereafter, 400 g of acetone was added and the solid deposited was filtered to obtain 18.8 g of the invention compound (f).

IR (KBr): Si—O—Si, 1020 cm$^{-1}$
$^1$H-NMR (CDCl$_3$):
 −0.15 ppm —CH$_2$—Si—$\underline{CH_3}$
 0.01 ppm —O—Si—$\underline{CH_3}$
 0.36 ppm —$\underline{CH_2}$—Si
 1.21 ppm —$\underline{CH_2}$—
 1.47 ppm —($\underline{CH_2}$)—CH$_2$—O—P, —O—CH$_2$—$\underline{CH_2}$—
 3.29 ppm —$\underline{CH_2}$—O—$\underline{CH_2}$—
 3.83 ppm —$\underline{CH_2}$—O—P
 $^{31}$P-NMR (CDCl$_3$):
 −13.95 ppm

Example 23

Organo(poly)siloxanes modified with polyvalent metal salt of phosphoric diester according to the present invention were tested with respect to the gel forming performance on cosmetic oil agents.

Evaluation method

The compounds shown in Table 3 were each dissolved in silicone oils for cosmetic use (octamethyl cyclotetrasiloxane or decamethyl cyclopentasilxane) at room temperature so as to be 2% by weight, and the state of the formed gel was visually evaluated according to the following criteria:

A: Thixotropic gel is formed.
B: Gel is formed, which does not show thixotropy.
C: Gel is not formed.

TABLE 3

| | Silicone oils | | |
|---|---|---|---|
| Added compounds | Octamethyl cycotetra- siloxane | Decamethyl cyclopenta- siloxane | Linear silicone oil (dimethylpoly- siloxane)*$^2$ |
| Compound (a) of the present invention | A | A | B |
| Compound (b) of the present invention | A | A | B |
| Compound (c) of the | A | A | B |

TABLE 3-continued

| | Silicone oils | | |
|---|---|---|---|
| Added compounds | Octamethyl cycotetra-siloxane | Decamethyl cyclopenta-siloxane | Linear silicone oil (dimethylpoly-siloxane)*[2] |
| present invention | | | |
| Compound (d) of the present invention | A | A | A |
| Compound (e) of the present invention | A | A | A |
| Compound (f) of the present invention | A | A | A |
| Compound (13-a) | C | C | C |
| Compound (13-b) | C | C | C |
| Compound (13-c) | C | C | C |
| No additive | C | C | C |
| Copolymer of organopolysiloxane*[1] | C | C | C |
| Calcium salt of $C_{16}$ phosphoric diester | C (insoluble) | C (insoluble) | C |

*[1]: Prepared by permeating a silicone oil into an organopolysiloxane polymer having a three dimensional cross-linked structure (polymer of an organohydrogen siloxane and an organopolysiloxane containing an aliphatic unsaturated group):

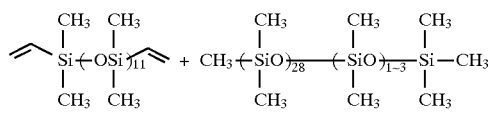

*[2]: CKF96A, product of Shin'etsu Kagaku Silicone K.K., Viscosity 6 cs.

As shown in Table 3, the compounds of the present invention all formed thixotropic gels on the silicone oils for cosmetic use.

Example 24

Oil-based detergent:
(Formulation)

| 1) Compound (a) of the present invention | 3 wt % |
|---|---|
| 2) Glyceryl polyoxyethylene (20) triisostearate | 10 |
| 3) Squalane | 40 |
| 4) Decamethyl cyclopentasiloxane | 47 |

(Process)

Components (1) to (4) were heated and uniformly dissolved with a disperser to obtain an oil-based detergent composition.

The obtained composition was stable and had excellent sensation during use. Moreover, no dripping or running down of liquid from fingers was occurred during use of the composition.

Example 25

Creamy foundation:

| 1) | Compound (b) of the present invention | 10 wt % |
|---|---|---|
| 2) | Dimethylpolysiloxane (6 cs) | 5 |
| 3) | Octamethyl cyclotetrasiloxane | 40 |
| 4) | Glycerol | 2 |
| 5) | Purified water | balance |
| 6) | Pigments: | |
| | Sericite | 6 |
| | Titanium oxide | 8 |
| | Iron oxide | 12 |
| 7) | Nylon powder | 5 |
| 8) | Dimethylpolysiloxane/polyoxyalkylene copolymer | 1 |

(Process)

Components (1) to (3) and (8) were heated and uniformly dissolved with a disperser, to which components (6) and (7) were added and further dispersed with a disperser. components (4) and (5) were added thereto while stirring for emulsification to obtain a creamy foundation.

The obtained foundation was stable and excellent in sensation during use. Moreover, no dripping or running down of liquid from fingers was occurred during use of the foundation.

Example 26

O/W cream:

| 1) Compound (c) of the present invention | 3 wt % |
|---|---|
| 2) Monocetyl phosphate | 0.5 |
| 3) Squalane | 2 |
| 4) Isopropyl parmitate | 2 |
| 5) Olive oil | 2 |
| 6) Dimethylpolysiloxane (6 cs) | 5 |
| 7) Octamethyl cyclotetrasiloxane | 10 |
| 8) Glycerol | 5 |
| 9) L-arginine | 0.5 |
| 10) Ethanol | 5 |
| 11) Purified water | balance |

(Process)

Components (1) to (7) were heated and uniformly dissolved with a disperser, to which components (8) to (11) were added while stirring for emulsification to obtain an O/W cream.

The obtained composition was stable and had excellent sensation during use. Moreover, no dripping or running down of liquid from fingers was occurred during use of the composition.

Example 27

Oil-based cosmetic cake:

| 1) | Compound (f) of the present invention | 6 wt % |
|---|---|---|
| 2) | Dimethylpolysiloxane (6 cs) | 40 |
| 3) | Pigments: | |
| | Sericite | 16 |
| | Titanium oxide | 16 |
| | Iron oxide | 3 |
| 4) | Nylon powder | 15 |
| 5) | Perfume | suitable amount |

(Process)

Components (1) to (4) were heated and uniformly dissolved with a disperser, to which component (5) was added and further dispersed with a disperser to obtain an oil-based cosmetic cake.

The obtained composition was stable and excellent in sensation during use. Moreover, no dripping or running down of liquid from fingers was occurred during use of the composition.

The polyvalent metal salts of phosphoric diesters and organo(poly)siloxanes modified with polyvalent metal salts of phosphoric diesters according to the present invention are capable of imparting thixotropic rheological property to oil ingredients and silicon oils which are utilized in various technical fields such as electric, electronics, automobiles, machines, medicines, cosmetics, fibers, papers, pulps, building materials, paints and in other technical fields, and of constituting gels which are highly safe, transparent, excellent in sensation during use and free of spinability, and thus they are very useful, particularly as materials for preparing cosmetic compositions and perfumery compositions.

Accordingly, the cosmetic compositions according to the present invention have excellent thixotropy despite their state as gel form and are easy in handling, and furthermore they are stable and excellent in sensation during use.

Also, the cosmetic compositions according to the present invention give no sticky feeling inherent in silicone oils even when used as cosmetic compositions containing the silicone oils, do not impair any their advantageous features such as refreshing sensation in use and volatility, are stable as time passes and are capable of preventing the running of liquid caused by abundantly containing silicone oils, and therefore they are remarkably useful.

We claim:

1. A polyvalent metal salt of phosphoric diester represented by formula (1):

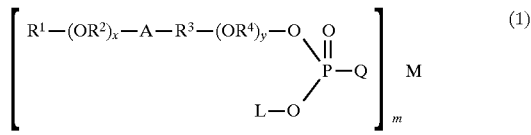

wherein $R^1$ represents a C1 to C20 linear or branched alkyl group, $R^2$ and $R^4$ are the same or different and independently represent a C2 to C3 linear or branched alkylene group, $R^3$ represents a C3 to C20 linear or C5 to C20 branched alkylene group, A represents a group —COO— or —O—, x and y are the same or different from each other and independently represent an integer of 0 to 10, L represents a C1 to C40 linear or branched alkyl group or a group, $R^1$—$(OR^2)_x$—A—$R^3$—$(OR^4)_y$— wherein $R^1$, $R^2$, $R^3$, $R^4$, A, x and y have the same meaning as defined hereinbefore, M represents a divalent or polyvalent metal ion, and m represents the same value as the valence of M.

2. The polyvalent metal salt of phosphoric diester according to claim 1, wherein at least one terminal of the alkyl groups represented by $R^1$ or L in formula (1) is $(CH_3)_3C$—.

3. The polyvalent metal salt of phosphoric diester according to claim 1, wherein M in formula (1) is $Ca^{2+}$ or $Al^{3+}$.

4. A method of preparing a polyvalent metal salt of phosphoric diester as defined in claim 1, which comprises reacting a phosphoric diester or a salt thereof represented by formula (2):

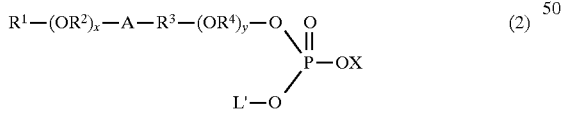

wherein $R^1$ represents a C1 to C20 linear or branched alkyl group, $R^2$ and $R^4$ are the same or different and independently represent a C2 to C3 linear or branched alkylene group, $R^3$ represents a C3 to C20 linear or C5 to C20 branched alkylene group, A represents a group —COO— or —O—, x and y are the same or different from each other and independently represent an integer of 0 to 10, L represents a C1 to C40 linear or branched alkyl group or a group, $R^1$—$(OR^2)_x$—A—$R^3$—$(OR^4)_y$— wherein $R^1$, $R^2$, $R^3$, $R^4$, A, x and y have the same meaning as defined hereinbefore, X represents a hydrogen, alkali metal, ammonium, alkylamine or alkanolamine; with a polyvalent metal salt represented by formula (3):

$$M_p Y_q \quad (3)$$

wherein X is a divalent or polyvalent metal ion, Y represents an organic or inorganic anion, p and q are integers which correspond to the valences of Y and m, respectively and are in the minimum ratio.

5. A phosphoric diester or a salt thereof represented by formula (2'):

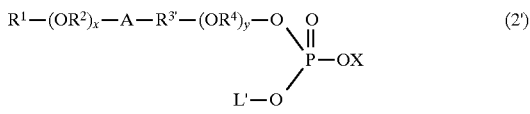

wherein $R^1$ represents a C1 to C20 linear or branched alkyl group, $R^2$ and $R^4$ are the same or different and independently represent a C2 to C3 linear or branched alkylene group, $R^{3'}$ represents a C7 to C20 linear or branched alkylene group, A represents a group —COO— or —O—, x and y are the same or different from each other and independently represent an integer of 0 to 10, L' represents a C1 to C40 linear or branched alkyl group or a group, $R^1$—$(OR^2)_x$—A—$R^{3'}$—$(OR^4)_y$— wherein $R^1$, $R^2$, $R^3$, $R^4$, A, x and y have the same meaning as defined herein before, X represents a hydrogen, alkali metal, ammonium, alkylamine or alkanolamine.

6. The phosphoric diester or its salt according to claim 5, wherein at least one terminal of the alkyl groups represented by $R^1$ or L' in formula (2') is $(CH_3)_3C$—.

7. A method of preparing a phosphoric diester or a salt thereof as defined in claim 5, which comprises reacting an alcohol represented by formula (4):

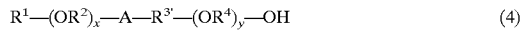

$$R^1—(OR^2)_x—A—R^{3'}—(OR^4)_y—OH \quad (4)$$

wherein $R^1$ represents a C1 to C20 linear or branched alkyl group, $R^2$ and $R^4$ are the same or different and independently represent a C2 to C3 linear or branched alkylene group, $R^{3'}$ represents a C7 to C20 linear or branched alkylene group, A represents a group —COO— or —O—, x and y are the same or different from each other and independently represent an integer of 0 to 10; or a mixture of an alcohol represented by formula (4) and an alcohol represented by formula (5):

$$L''—OH \quad (5)$$

wherein L" represents a C1 to C40 linear or branched alkyl group; with a phosphorylating agent, and optionally neutralizing with a monovalent base.

8. A gelling composition which comprises a polyvalent metal salt of phosphoric diester as defined in claim 1 and an oil.

9. A cosmetic composition which comprises a polyvalent metal salt of phosphoric diester as defined in claim 1 and an oil.

10. An organo(poly)siloxane modified with a polyvalent metal salt of phosphoric diester which comprises the structural units represented by formulae (9) and (10):

$$-\underset{\underset{R^8}{|}}{\overset{\overset{R^7}{|}}{Si}O-}\underset{CH_2CH_2-R^6-(OR^5)_p-O}{\overset{CH_2CH_2-R^6-(OR^5)_p-O}{\diagdown}}\overset{O}{\underset{\diagup}{\overset{||}{P}}}-O^-.(M^{n+})1/n \quad (9)$$

$$-\underset{\underset{R^{10}}{|}}{\overset{\overset{R^9}{|}}{Si}}-(O)_w- \quad (10)$$

wherein $R^5$: a C2 to C20 alkylene group, $R^6$: a C1 to C50 linear or branched alkylene group which may optionally be substituted by a hydroxyl group, p: a number from 0 to 200, M: a divalent or polyvalent metal atom, n: a number same as the value of the valence of M, $R^7$, $R^8$, $R^9$, $R^{10}$: independently represent a hydrogen atom, an alkyl group, an alkoxy group, a phenyl group or a structural unit represented by formula (10), and w: a number of 0 or 1.

11. An organo(poly)siloxane modified with a polyvalent metal salt of phosphoric diester represented by formula (11):

$$(11)$$

(structural formula with $R^{11}$ through $R^{28}$, (OSi)_q, (OSi)_r, (OSi)_s, (OSi)_t, (OSi)_u, (OSi)_v groups and $CH_2CH_2-R^6-(OR^5)_p-O$ phosphate diester group)

wherein $R^5$: a C2 to C20 alkylene group, $R^6$: a C1 to C50 linear or branched alkylene group which may optionally be substituted by a hydroxyl group, p: a number from 0 to 200, M: an alkaline earth metal atom or a divalent or polyvalent transition metal atom, n: a number same as the value of the valence of M, $R^{11}$ to $R^{28}$: independently represent a C1 to C22 alkyl or alkoxy group, or a phenyl group, among which $R^{15}$ and $R^{24}$ may join to form a divalent oxygen atom, q, r, s, t, u, v: independently represent a number from 0 to 1000.

12. A method of preparing an organo(poly)siloxane modified with a polyvalent metal salt of phosphoric diester as defined in claim 10, which comprises reacting an organo (poly)siloxane having the structural units represented by formulae (12) and (10):

$$-\underset{\underset{H}{|}}{\overset{\overset{R^7}{|}}{Si}O-} \quad (12)$$

$$-\underset{\underset{R^{10}}{|}}{\overset{\overset{R^9}{|}}{Si}}-(O)_w- \quad (10)$$

wherein $R^7$, $R^9$ and $R^{10}$ independently represent a hydrogen, alkyl, alkoxy, phenyl or a structural unit represented by formula (10); with a polyvalent metal salt of phosphoric diester containing an unsaturated group represented by formula (13):

$$\underset{CH_2=CH-R^6-(OR^5)_p-O}{\overset{CH_2=CH-R^6-(OR^5)_p-O}{\diagdown}}\overset{O}{\underset{\diagup}{\overset{||}{P}}}-O^-.(M^{n+})1/n \quad (13)$$

wherein $R^5$: a C2 to C20 alkylene group, $R^6$: a C1 to C50 linear or branched alkylene group which may optionally be substituted by a hydroxyl group, p: a number from 0 to 200, M: a divalent or polyvalent metal atom, n: a number same as the value of the valence of M.

13. A gelling composition which comprises an organo (poly)siloxane modified with polyvalent metal salt of phosphoric diester as defined in claim 10 and an oil.

14. A cosmetic composition which comprises an organo (poly)siloxane modified with polyvalent metal salt of phosphoric diester as defined in claim 10 and an oil.

15. A gelling composition which comprises an organo (poly)siloxane modified with the polyvalent metal salt of phosphoric diester as defined in claim 11 and an oil.

16. A cosmetic composition which comprises an organo (poly)siloxane modified with the polyvalent metal salt of phosphoric diester as defined in claim 11 and an oil.

17. A polyvalent metal salt of phosphoric diester represented by formula (1-21):

$$\left[\left(\ \diagup\!\!\diagdown\!\!-O\!\!\frown\!\!\smile\!\!\frown\!\!\smile\!\!-O\right)_2\overset{O}{\underset{||}{P}}O\right]_3 Al. \quad (1-21)$$

18. A gelling agent comprising the polyvalent metal salt of phosphoric diester as claimed in claim 17.

19. A cosmetic composition comprising the polyvalent metal salt of phosphoric diester as claimed in claim 17.

* * * * *

UNITED STATES PATENT AND TRADEMARK OFFICE
CERTIFICATE OF CORRECTION

PATENT NO. : 5,872,272

DATED : February 16, 1999

INVENTOR(S): Shinji Yano, et al.

It is certified that an error appears in the above-identified patent and that said Letters Patent is hereby corrected as shown below:

Column 35, Line 23, " 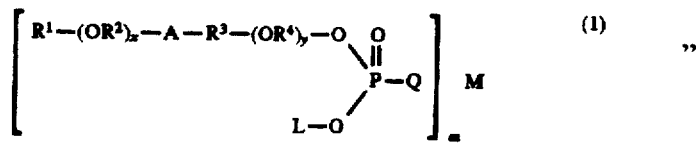 "

should read -- 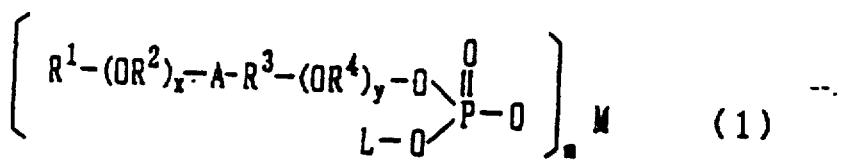 --.

Signed and Sealed this

Thirty-first Day of August, 1999

*Attest:*

Q. TODD DICKINSON

*Attesting Officer*     *Acting Commissioner of Patents and Trademarks*